(12) United States Patent
Li et al.

(10) Patent No.: US 6,444,011 B2
(45) Date of Patent: Sep. 3, 2002

(54) PROCESS AND SYSTEM FOR SEPARATION AND RECOVERY OF PERFLUOROCOMPOUND GASES

(75) Inventors: Yao-En Li, Buffalo Grove; Jospeh E. Paganessi, Burr Ridge; David Vassallo, Glenview, all of IL (US); Gregory K. Fleming, Wilmington, DE (US)

(73) Assignee: American Air Liqide, Inc., Fremont, CA (US)

( * ) Notice: Subject to any disclaimer, the term of this patent is extended or adjusted under 35 U.S.C. 154(b) by 0 days.

(21) Appl. No.: 09/768,262

(22) Filed: Jan. 25, 2001

Related U.S. Application Data

(63) Continuation of application No. 09/119,453, filed on Jul. 21, 1998, now Pat. No. 6,214,089, which is a continuation of application No. 08/665,142, filed on Jun. 14, 1996, now Pat. No. 5,785,741, which is a continuation-in-part of application No. 08/503,325, filed on Jul. 15, 1995, now abandoned.

(51) Int. Cl.[7] .................. B01D 53/22; B01D 53/04; B01D 3/00; B01D 5/00
(52) U.S. Cl. .................. 95/45; 95/47; 95/53; 95/90; 95/149; 95/288
(58) Field of Search ................ 95/45, 47–49, 95/51–54, 90, 92, 149, 230, 237; 96/4, 7–14, 108, 134, 361

(56) References Cited

U.S. PATENT DOCUMENTS

| | | | |
|---|---|---|---|
| 2,947,687 A | 8/1960 | Lee | 210/640 |
| 2,953,502 A | 9/1960 | Binning et al. | 202/42 |
| 2,960,462 A | 11/1960 | Lee et al. | 210/500.29 X |

(List continued on next page.)

FOREIGN PATENT DOCUMENTS

| | | |
|---|---|---|
| EP | 0 171 879 | 2/1986 |
| EP | 0 239 190 | 9/1987 |
| EP | 0 358 915 | 3/1990 |
| EP | 0 389 126 | 9/1990 |
| EP | 0 521 784 | 1/1993 |
| JP | 61-187918 | 8/1986 |
| JP | 63-126522 | 5/1988 |
| JP | 4-322716 | 11/1991 |
| JP | 3-284335 | 12/1991 |
| JP | 4-016213 | 1/1992 |
| JP | 6-254367 | 9/1994 |
| WO | 90/15662 | 12/1990 |

OTHER PUBLICATIONS

Michael T. Mocella, "Perfluorocompound Emission Reduction from Semiconductor Processing Tools: An Overview of Options and Strategies," Global Warming Symposium, Dallas, TX, Jun. 7–8, 1994.

Larry Anderson, "Vector Technology's Phoenix Combustor," Global Warming Symposium, Dallas, TX, Jun. 7–8, 1994.

AT&T, Microelectronics and Novapure Corp., "PFC Concentration and Recycle," Global Warming Symposium, Dallas, TX, Jun. 7–8, 1994.

(List continued on next page.)

*Primary Examiner*—Robert H. Spitzer
(74) *Attorney, Agent, or Firm*—Linda K. Russell

(57) ABSTRACT

Processes and systems to recover at least one perfluorocompound gas from a gas mixture are provided. In one embodiment the inventive process comprises the steps of a) providing a gas mixture comprising at least one perfluorocompound gas and at least one carrier gas, the gas mixture being at a predetermined pressure; b) providing at least once glassy polymer membrane having a feed side and a permeate side; c) contacting the feed side of the at least one membrane with the gas mixture; d) withdrawing from the feed side of the membrane as a non-permeate stream at a pressure which is substantially equal to the predetermined pressure a concentrated gas mixture comprising essentially the at least one perfluorocompound gas; and e) withdrawing from the permeate side of the membrane as a permeate stream a depleted gas mixture comprising essentially the at least one carrier gas.

7 Claims, 12 Drawing Sheets

U.S. PATENT DOCUMENTS

| | | | |
|---|---|---|---|
| 2,970,106 A | 1/1961 | Binning et al. | 208/347 |
| 3,508,994 A | 4/1970 | Nyrop | 156/280 |
| 3,616,607 A | 11/1971 | Klass et al. | 55/16 |
| 3,648,845 A | 3/1972 | Riley | 210/500.29 X |
| 4,086,310 A | 4/1978 | Bottenbruch et al. | 264/41 |
| 4,113,628 A | 9/1978 | Alegranti | 210/500 M |
| 4,119,417 A * | 10/1978 | Heki et al. | 55/158 |
| 4,132,824 A | 1/1979 | Kimura et al. | 428/220 |
| 4,155,793 A | 5/1979 | Salemme et al. | 156/246 |
| 4,156,597 A | 5/1979 | Browall | 55/16 |
| 4,178,224 A | 12/1979 | Porter | 204/237 |
| 4,192,824 A | 3/1980 | Robinson et al. | 585/409 |
| 4,378,324 A | 3/1983 | Makino et al. | 264/41 |
| 4,424,067 A | 1/1984 | Tarasenko et al. | 95/48 |
| 4,460,526 A | 7/1984 | Makino et al. | 264/41 |
| 4,474,662 A | 10/1984 | Makino et al. | 210/500.2 |
| 4,485,056 A | 11/1984 | Makino et al. | 264/41 |
| 4,512,893 A | 4/1985 | Makino et al. | 210/500.2 |
| 4,553,983 A | 11/1985 | Baker | 55/16 |
| 4,602,922 A | 7/1986 | Cabasso et al. | 55/158 |
| 4,664,669 A | 5/1987 | Ohyabu et al. | 623/66 |
| 4,689,267 A | 8/1987 | Takamizawa et al. | 428/376 |
| 4,701,187 A | 10/1987 | Choe et al. | 95/54 X |
| 4,713,292 A | 12/1987 | Takemura et al. | 428/373 |
| 4,714,481 A | 12/1987 | Matsuura et al. | 55/158 |
| 4,717,394 A | 1/1988 | Hayes | 55/16 |
| 4,741,829 A | 5/1988 | Takemura et al. | 210/500.23 |
| 4,743,435 A | 5/1988 | Kitahara et al. | 423/210 |
| 4,756,932 A | 7/1988 | Puri | 427/175 |
| 4,784,837 A | 11/1988 | Kitayama et al. | 423/210 |
| 4,826,599 A | 5/1989 | Bikson et al. | 210/500.3 |
| 4,880,441 A | 11/1989 | Kesting et al. | 95/47 |
| 4,881,953 A | 11/1989 | Prasad et al. | 95/54 X |
| 4,910,001 A | 3/1990 | Kitahara et al. | 423/210 |
| 4,941,893 A | 7/1990 | Hsieh et al. | 55/16 |
| 4,957,513 A | 9/1990 | St. Hilaire | 55/16 |
| 4,988,371 A | 1/1991 | Jeanes et al. | 95/53 |
| 4,996,030 A | 2/1991 | Kitahara et al. | 423/210 |
| 5,009,869 A | 4/1991 | Weinberg et al. | 95/45 X |
| 5,051,114 A | 9/1991 | Nemser et al. | 95/47 |
| 5,064,447 A | 11/1991 | Lee | 95/48 |
| 5,085,676 A | 2/1992 | Ekiner et al. | 55/158 |
| 5,182,088 A | 1/1993 | Leondaridis et al. | 423/210 |
| 5,196,616 A | 3/1993 | Lee et al. | 95/48 X |
| 5,226,932 A | 7/1993 | Prasad | 95/45 |
| 5,240,471 A | 8/1993 | Barbe et al. | 95/54 |
| 5,256,295 A | 10/1993 | Baker et al. | 95/45 X |
| 5,256,296 A | 10/1993 | Baker et al. | 210/640 |
| 5,281,253 A | 1/1994 | Thompson | 95/45 X |
| 5,281,255 A | 1/1994 | Toy et al. | 95/50 |
| 5,282,964 A | 2/1994 | Young et al. | 95/45 X |
| 5,282,969 A | 2/1994 | Xu | 95/45 X |
| 5,288,304 A | 2/1994 | Koros et al. | 95/45 |
| 5,290,341 A | 3/1994 | Barbe | 95/54 |
| 5,378,439 A | 1/1995 | Delobel et al. | 423/210 |
| 5,383,956 A | 1/1995 | Prasad et al. | 95/45 |
| 5,383,957 A | 1/1995 | Barbe et al. | 96/8 |
| 5,429,662 A | 7/1995 | Fillet | 95/45 X |
| 5,538,536 A | 7/1996 | Fuentes et al. | 95/45 |
| 5,618,332 A | 4/1997 | Ekiner et al. | 95/51 |
| 5,730,779 A | 3/1998 | Chernyakov et al. | 95/45 |
| 5,759,237 A | 6/1998 | Li et al. | 95/41 |
| 5,779,763 A | 7/1998 | Pinnau et al. | 95/34 |
| 5,785,741 A | 7/1998 | Li et al. | 96/4 |
| 5,814,127 A | 9/1998 | Li | 95/47 |
| 5,843,208 A | 12/1998 | Anumakonda et al. | 95/47 |
| 5,855,647 A | 1/1999 | Li et al. | 95/45 |
| 5,858,065 A | 1/1999 | Li et al. | 95/45 |
| 5,858,066 A | 1/1999 | O'Brien et al. | 95/48 |
| 5,919,285 A | 7/1999 | Li et al. | 95/45 |
| 5,976,222 A * | 11/1999 | Yang et al. | 95/45 |
| 6,032,484 A | 3/2000 | Chernyakov et al. | 62/624 |
| 6,214,089 B1 * | 4/2001 | Li et al. | 95/45 |

OTHER PUBLICATIONS

Air Liquide America Corporation, "Solval™ Solvent Condensation and Recovery, System," Technical Bulletin, 1994.

Shan–Tao Hsieh and George E. Keller, II, "Separation of Hydrogen From Silan Via Membranes: A Step in the Production of Ultra–High–Purity Silicon," *Journal of Membrane Science*, 70 (1992) pp. 143–152.

Japanese Abstract Only JP60022902, from the European Patent Office Abstract 85–066277.

William M. Carson; Kimberly A. Christian; Eugene C. Crossland; Thomas H. Hsiung; Robert G. Ridgeway; and James H. Yang, "large Scale PFC Capture System," (Air Products and Chemicals, Inc.) presented at Semicon Southwest, Austin, TX, Oct. 13, 1997.

V. Stannett and J.L. Williams, "The Permeability of Poly-(ethyl Methacrylate) to Gases and Water Vapor" *Journal of Polymer Science*: Part C, No. 10, pp. 45–49, (1965).

Francis J. Norton, "Gas Permeation through Lexan Polycarbonate Resin," *Journal of Applied Polymer Science*, vol. 7, pp. 1649–1659, (1963).

*Polymeric Gas Separation Membranes*, edited by D.R. Paul and Yuri P. Yampol'skii, CRC Press, Inc., 1994, pp. 186–189, 202, 206, 364, 365, 397.

*Chemical Mechanical Technology 41*, "New Development of High–Level Separation," edited by Kagaku Kogaku Kai, published by San–ei Shuppan, May 20, 1989 (partial translation provided), pp. 276–281.

R. Rautenbach and K. Welsch, "Treatment of landfill gas by gas permeation—pilot plant results and comparison to alternatives," published by Elsevier Science Publishers B.V., *Desalination*, 90 (1993), pp. 193–197.

*JSME Mechanical Engineers' Handbook*, edited by Nihon Kikai Gakkai, Apr. 15, 1987, pp. 114–117.

*Basic Principles of Membrane Technology*, Marcel Mulder, Kluwer Academic Publishers, 1991, pp. 318–324.

*Latest Membrane Treatment Technology and Application Thereof*, edited by Hiroshi Shimizu and Masato Nisihmura (supervisors), published by Fuji Technosystem, Aug. 1, 1984, pp. 275–279 (partial translation provided).

* cited by examiner

PROCESS AND SYSTEM FOR SEPARATION AND RECOVERY OF PERFLUOROCOMPOUND GASES

CROSS-REFERENCE TO RELATED APPLICATIONS

This application is a continuation of Application Ser. No. 09/119,453, filed on Jul. 21, 1998, now U.S. Pat. No. 6,214,089, which is a continuation of Application Ser. No. 08/665,142, filed on Jun. 14, 1996 (now U.S. Pat. No. 5,785,741), which is a continuation-in-part of Application Ser. No. 08/503,325, filed on Jul. 15, 1995 (now abandoned).

BACKGROUND OF THE INVENTION

1. Field of the Invention

The invention relates to gas separation processes and more particularly the separation and recovery (or disposal) of perfluorocompound gases from a gas mixture. Especially, the invention relates to the concentrating of low concentration gas mixtures of perfluorocompound gases such as those present in the effluent of a semiconductor manufacturing process, particularly the etching and cleaning steps.

2. Related Art

The semiconductor industry is now using extensively perfluorocompounds such as $CF_4$, $C_2F_6$, $C_3F_8$, $C_4F_{10}$, $CHF_3$, $SF_6$, $NF_3$, and the like, in the semiconductor manufacturing processes involving gases, particularly in the various etching steps of the semiconductor manufacturing processes as well as in the chamber cleaning step of the manufacturing process. Those perfluorocompound gases are used either pure or diluted, for example with air or nitrogen or other inert gas or in admixture with other perfluorocompound gases or other carrier gases (for example inert gases). All of those gases do not necessarily react with other species during the manufacturing processes: accordingly, when reactors are cleaned or evacuated to carry out another step of the manufacturing process, the effluent gases or gas mixtures should not be vented, even if they are largely diluted with air or any other gas such as inert gas. Most of the perfluorocompounds (also called PFCs) have lifetimes measured in thousands of years in the atmosphere and are also strong infrared absorbers. In the "Global Warming Symposium" held on Jun. 7-8, 1994, in Dallas, Tex., USA, carbon tetrafluoride ($CF_4$), hexafluoroethane ($C_2F_6$), nitrogen trifluoride ($NF_3$), and sulfur hexafluoride ($SF_6$) have been identified as greenhouse gases of concern to the semiconductor industry.

In the presentation made at this symposium by Michael T. Mocella and entitled "Perfluorocompound Emission Reduction From Semiconductor Processing Tools: An Overview Of Options And Strategies", the various possible strategies to control emission of these gases in the atmosphere were explained.

Apart from process replacement by non PFCs, several methods are already known or under development:

chemical-thermal decomposition with various activated metals wherein the spent bed material must be disposed. It is presently considered as commercially unproven even if it is under promising development.

combustion-based decomposition process (or chemical-thermal process) using a flame to supply both the thermal energy and the reactants for the decomposition. There are some safety issues associated with the hydrogen or natural gas fuels used and all the PFCs will produce HF as a combustion product (if the temperature is high enough), whose emissions are also of concern and must be dealt with also. High temperatures may also be generated using a resistance heater.

plasma-based decomposition process which involves the use of a plasma such as coupled radio frequency systems to partially decompose $C_2F_6$, with over 90% decomposition of $C_2F_6$. However, such systems are not yet commercially proven. Oxygen is usually needed to drive the decomposition to non PFC products with, however, the generation of BF which needs to be thereafter managed.

recovery process wherein the PFCs are recovered instead of being destroyed in order to be recycled. This kind of process is of a great interest because it is considered as the "greenest" one. Different schemes, according to the author, are possible "based on combinations of adsorption or low temperature trapping of PFCs". There are, however, several challenges such as dealing with the large amount of nitrogen associated with the pump operation, the close boiling points of $CF_4$ and $NF_3$, the mixing of various process streams and/or possible reactions with adsorbents. While recycle is suggested, there are obvious questions about recycling such mixtures.

Another combustion system for destroying high nitrogen content effluent gas streams comprising PFCs is disclosed in the article entitled "Vector Technology's Phoenix Combustor" by Larry Anderson presented at the same symposium Jun. 7–8, 1994. This abatement system also uses a gas flame (using natural gas or hydrogen with air), which leads then to the same problem of HF generation and further destruction (plus the generation of $NO_x$, $CO_2$ inherent to any combustion process).

In the article presented at the same symposium by AT&T Microelectronics and Novapure Corporation and entitled "PFC Concentration and Recycle", the authors acknowledge the advantages of the recovery processes which avoid production of carbon dioxide, $NO_x$ and BF (compared to combustion processes). Briefly, this process is disclosed as the use of a dual bed adsorber (activated carbon), wherein one of the beds is in the adsorption mode, while the second bed is regenerated: the PFCs are adsorbed on the carbon sieves while the "carrier" gases, such as nitrogen, hydrogen are not adsorbed and are vented to the exhaust system. When the system is switched on the second adsorber, then the first one is evacuated using a vacuum pump, then the effluent is recompressed and the PFC gas mixture is recovered. One of the issues not yet resolved with such a system is that $CF_4$, which is non polar, is not readily adsorbed by the carbon sieve and is then rejected with the vent gases. Also, any adsorption system is very sensitive to moisture and any trace of water has to be removed from the feed flow.

It is also known from U.S. Pat. No. 5,281,255 to use membranes made of rubbery polymers such as poly dimethyl siloxane or certain particular polymers such as a substituted polyacethylene (having a low glass transition temperature), to recover condensable organic components having a boiling point higher than −50° C., essentially hydrocarbons ($CH_4$, $C_2H_6$, and the like), said hydrocarbons having the property of permeating through said membranes much faster than air, and then recovering on the permeate side of the membrane said hydrocarbons. The permeate (hydrocarbons) is then recovered at either substantially atmospheric pressure or lower pressure while the non-permeate (e.g. air) is still at the original pressure of the feed stream but is vented, and all of the pressure energy of the feed stream is lost.

Also, it is disclosed in U.S. Pat. No. 5,051,114 a selectively permeable membrane formed from an amorphous polymer of perfluoro 2-2 dimethyl 1-3-dioxole which is usable for separation of hydrocarbons or chlorofluorocarbons from, for example, air. Such a particular membrane apparently permeates oxygen and nitrogen faster than hydrocarbons and chlorofluorocarbons which can be recovered unexpectedly on the non-permeate side of the membrane, contrary to all of the membranes, including those disclosed in U.S. Pat. Nos. 4,553,983 and 5,281,255. In the '114 patent, there is also disclosed a mixture of the amorphous polymer of perfluoro 2-2 dimethyl 1-3 dioxole and polytetrafluoroethylene. All these perfluoro polymers are known to be resistant to most of the harmful chlorofluorocarbons and hydrocarbons which make them commercially suitable for such separation. However, this membrane is not currently available and there is no indication in this patent whether or not such a membrane is suitable for separation of PFCs from air or nitrogen particularly at low concentrations of PFCs in carrier gases, and at widely varying feed flow conditions.

There is still presently a need for a "green" process for concentration and/or recovery of PFCs from a gaseous stream, which can be used with a feed flow comprising or saturated with, moisture, which can handle safely the PFCs recovery and/or concentration even with important or extreme variations of flows and/or concentration of PFCs in the feed stream, which does not produce hydrofluoric acid (HF) as a residue from the destruction of the PFCs (in addition to the possible HF content of the feed).

SUMMARY OF THE INVENTION

It has now been unexpectedly found that effluent gases, for example, from a semiconductor manufacturing process, which comprise perfluorocompounds can be treated efficiently by using certain, preferably hollow fiber, membranes which permeate much faster the "carrier gases" of the effluent gas mixture, such as air, nitrogen, oxygen, argon and/or helium, than the PFCs of the gas mixture which are then recovered on the non-permeate side of the membrane.

Preferred membranes are glassy polymeric membranes, more preferably asymmetric or composite (with an asymmetric outer layer) membranes. Preferably, these glassy polymeric membranes do not include perfluorinated membranes. However, the glassy polymeric membranes used in accordance with the invention can comprise a layer, including a posttreatment layer as disclosed in U.S. Ser. No. 08/138,309 filed Oct. 21, 1993 (now abandoned), and which is incorporated herein by reference, made of a fluorinated polymer such as polytetrafluoroethylene, amorphous perfluoro 2-2 dimethyl 1-3 dioxide, and the like.

One aspect of the invention relates to a process to recover at least one perfluorocompound gas from a gas mixture, comprising the steps of:

a) providing a gas mixture comprising at least one perfluorocompound gas and at least one carrier gas, the gas mixture being at a predetermined pressure;

b) providing at least one glassy polymer membrane having a feed side and a permeate side, the membrane being permeable to the at least one carrier gas and being non-permeable to the at least one perfluorocompound gaseous species;

c) contacting the feed side of the at least one membrane with the gas mixture;

d) withdrawing from the feed side of the membrane as a first non-permeate stream at a pressure which is substantially equal to the predetermined pressure, a concentrated gas mixture comprising essentially the at least one perfluorocompound gas, and e) withdrawing from the permeate side of the at least one membrane as a permeate stream a depleted gas mixture consisting essentially of the at least one carrier gas.

According to another aspect, the invention also relates to a process to recover a perfluorocompound gas or gas mixture from a gas mixture flowing out from a semiconductor manufacturing process, comprising the steps of pretreating the gas mixture to substantially remove most of the harmful components (gas, particles, and the like) to the membrane and delivering a pretreated gas mixture, providing at least one glassy polymer membrane having a feed side and a permeate side, contacting the feed side of the membrane with the pretreated gas mixture at a first pressure, withdrawing the perfluorocompound gas or gas mixture from the feed side of the membrane at a pressure which is substantially equal to the first pressure and withdrawing a residue gas at a second pressure which is lower than the first pressure from the permeate side of the membrane. The semiconductor manufacturing process using PFCs may be selected from etching processes including oxide, metal and dielectric; deposition processes including silicon CVD, tungsten backetching, dry chamber cleaning, and the like.

As some of the glassy membranes are sensitive to certain products which may be harmful for them, i.e. which may destroy or plug them quickly, it is preferred to scrub the gas mixture prior to sending it on the membrane. Preferably any kind of species which is present in the feed flow stream which may harm the membrane is removed by the scrubber means, including any harmful gaseous HF, $NH_3$, $WF_6$, $O_3$, $BCl_3$, and any corrosive species, also any pyrophoric species including silicon hydrides such as $SiH_4$, and any particulates having average diameter greater than about 20 micrometers, and any oil mists. Indeed, it is preferred that compressors used in the methods and systems of the invention be sealed and oil-free.

One preferred aspect of the invention relates to a process to recover at least one perfluorocompound gas or gas mixture, comprising the steps of:

a) providing a glassy polymer membrane having a feed side and a permeate side;

b) providing a gas mixture at a first pressure comprising at least one perfluorocompound gaseous species, at least one harmful species for the membrane, and at least one carrier gas;

c) treating said gas mixture in scrubber means in order to substantially remove harmful species for said membrane and reduce the concentration of said harmful species to an acceptable level for said membrane and receiving a scrubbed gas mixture at a second pressure;

d) contacting the feed side of said membrane with said scrubbed gas mixture at substantially said second pressure or at a higher pressure;

e) withdrawing a concentrated gas mixture comprising a higher concentration of the at least one perfluorocompound gas than in the scrubbed gas mixture, from the feed side of the membrane as a non-permeate stream at a pressure which is substantially equal to said second pressure; and f) withdrawing a depleted gas or gas mixture from the permeate side of said membrane as a permeate stream which is enriched in a carrier gas and depleted in the at least one perfluorocompound at a third pressure.

According to a preferred aspect of the invention, after concentrating the PFCs with a membrane, the various PFCs are separated from each other, by well known methods per se, such as selective condensation or adsorption in order to recover either separate PFCs or mixtures of PFCs having close boiling points. According to another aspect of the invention, the PFCs gas mixture is concentrated again, for example, with a second membrane, or the PFCs gas mixture is stored or recycled in the process (with or without additional treatment).

Other preferred process and system aspects of the invention include provision of a vacuum pump, heat exchanger, compressor, or cryogenic pump in order that the PFC gas mixture may be compressed, at least partially liquefied, and stored for future use. Another feature of the invention includes the provision of a process step where the PFC gas mixture is concentrated using a plurality of membranes arranged in series, with the possibility of the concentrated PFC gas mixture from each membrane unit being capable of use as a sweep gas of the permeate side of any one of or all of the membrane units in the series. A further aspect of the invention is the provision of a PFC gas mixture surge tank prior to the PFCs being recycled into the semiconductor manufacturing process, or prior to being routed to storage.

Another aspect of the invention is a semiconductor manufacturing system comprising:

a) at least one reactor chamber adapted to receive perfluorocompound gases, carrier gases, and the like, the reactor chamber having a reactor effluent gas conduit attached thereto;

b) at least one glassy polymer membrane separation unit having a feed side and a permeate side, the membrane being permeable to at least one carrier gas and being substantially non-permeable to at least one perfluorocompound gas, the membrane unit connected to the reactor chamber via the reactor effluent conduit, the membrane unit having a permeate vent conduit and a non-permeate conduit, the latter adapted to direct at least a portion of a perfluorocompound containing non-permeate stream from the membrane unit to the reactor chamber. Preferred systems in accordance with the invention include provision of pretreatment and/or post-treatment means, such as dry or wet, (or both) scrubbers, thermal decomposers, catalytic decomposers, plasma gas decomposers and various filters as herein disclosed, prior to the reactor effluent stream entering the membrane unit. Also as herein disclosed, a plurality of membrane units may be arranged in series, either with or without provision of sweep gas of non-permeate on the permeate side of one or all membranes. Further preferred embodiments of systems of the invention included a damper or surge tank in the non-permeate conduit (i.e. between the first or plurality of membrane units and the reactor chamber); and the provision of a compressor, heat exchanger, cryogenic pump or vacuum pump on one or more of the non-permeate, PFC enriched stream(s), allowing the PFC enriched stream(s) to be stored in liquid form for future use. Also preferred are appropriate valves which allow the damper or surge tank, and the compressor for creating the liquid PFC mixture, to be bypassed, as explained more fully herein.

Preferred processes and systems of the invention include operating one or more of the membrane units at a constant concentration set-point for the PFC concentration in the non-permeate stream from each membrane unit. In this preferred system and process, the set-point concentration of the PFC in the non-permeate stream from each succeeding PFC membrane separation unit would of course be higher than the immediately preceding one. Appropriate sensors can be inserted into the non-permeate effluent conduit from each membrane unit to continuously or non-continuously analyze for PFC concentration, or, samples may be taken periodically or continuously from the non-permeate effluent from each membrane unit, which may be sent to dedicated analyzers either on-site or off-site. This information is preferably then forwarded to a process controller which may control for example the pressure of the feed to each membrane unit, temperature, flow, and the like. Also, when discussing the use of a sweep gas arrangement, the sweep gas may either be controlled via an open loop or a closed loop arrangement.

Another preferred system and process embodiment of the present invention includes the recycle of the permeate stream of either the first or succeeding stages of the membrane units (in other words, the carrier gas and other process gases are recycled). The carrier gases may be recycled directly to the reactor chambers, or may be delivered to heat exchangers, compressors, and the like to reduce them to liquid form for storage or future use. A recycle membrane may be provided, functioning to separate carrier gases from process gases.

Other preferred processes and systems of the invention are those wherein a waste stream from a pretreatment step for the gas mixture emanating from the semiconductor process is used to generate one or more perfluorocompounds or other chemicals, which may then be purified for use in the semiconductor process, or other chemical processes, as more specifically described in assignee's copending application Ser. No. 08/666,694 filed Jun. 14, 1996, which is incorporated herein by reference.

Still other preferred processes and systems in accordance with the invention are those wherein one or more non-permeate streams is post-treated to remove non-perfluorocompounds. Post-treatment methods include those previously mentioned as suitable for pretreatment of the feed gas to the membrane.

Another aspect of the invention is a method of recovery of a relatively pure PFC stream from a vent stream from one or more gas cabinets, tube trailers, clean rooms, or the like using a membrane unit as described herein.

Further understanding of the processes and systems of the invention will be understood with reference to the brief description of the drawing and detailed description which follows herein.

DESCRIPTION OF PREFERRED EMBODIMENTS

Figure 1:
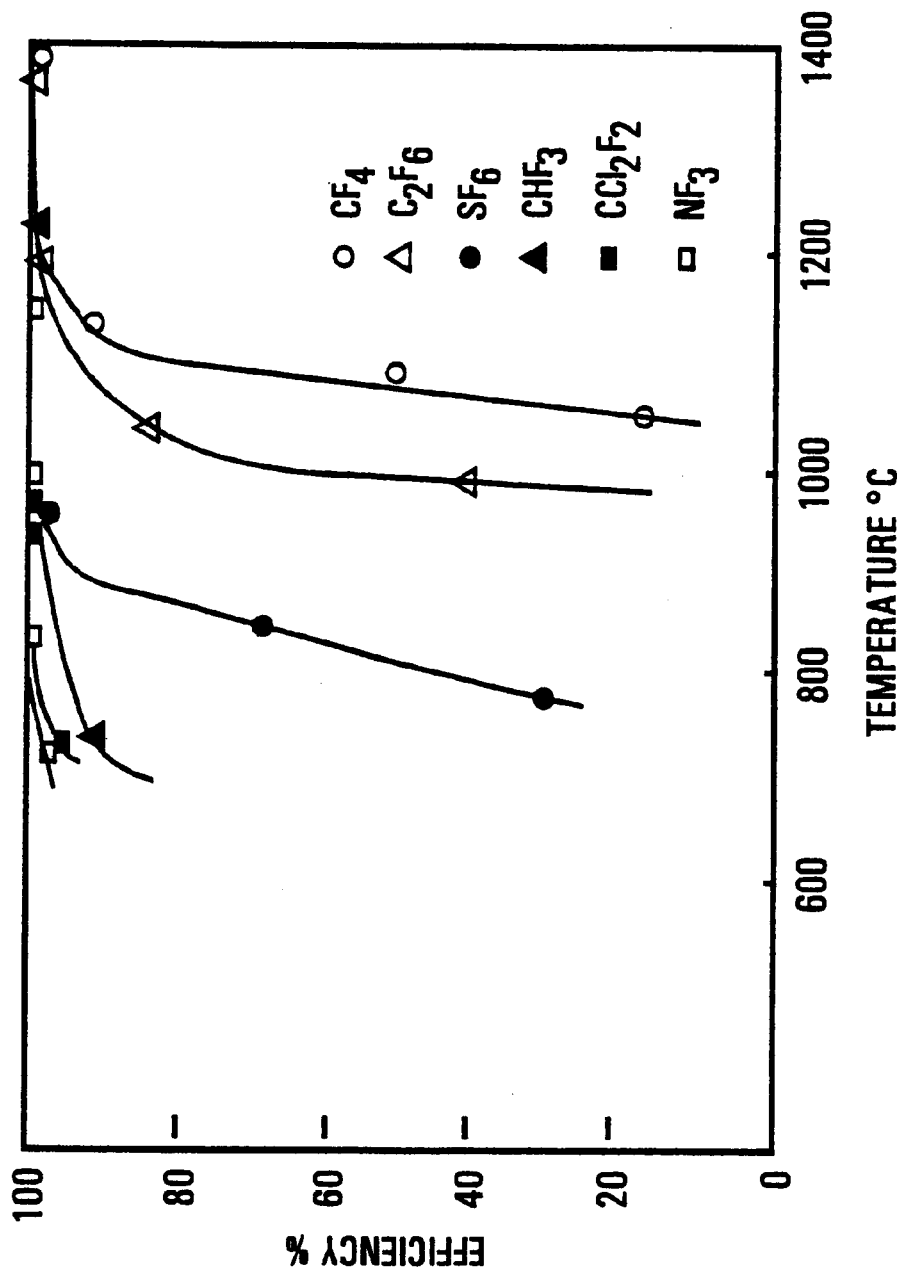
FIG. 1 is a graph illustrating the efficacy of destruction of PFCs with a burner versus the burner flame temperature (prior art)

Recovery of PFCs, for example, from a semiconductor manufacturing process, is now made possible by the present invention using certain types of polymer membranes and concentrating a gas mixture comprising PFCs by recovering the non-permeate flow on the non-permeate side of the membrane, while non harmful gases for the environment permeate through the membrane and can then be directly vented or recycled. This process is simpler and environmentally friendlier than many existing processes, as described hereabove. The non-permeate stream may either be rerouted to the semiconductor manufacturing reaction chamber, routed to a storage facility for future use, or routed to a PFC recovery apparatus for separation of individual or like PFCs, either on-site or off-site prior to reuse.

Perfluorocompounds, for the purpose of this invention, are defined as compounds comprising C, S and/or N atoms wherein all or all but one hydrogen have been replaced by fluorine. The most common PFCs include, without being limited to, any of the following compounds: fully fluorinated hydrocarbons such as $CF_4$, $C_2F_6$, $C_3F_8$, $C_4F_{10}$, and other fluorinated compounds such as $CHF_3$, $SF_6$, $NF_3$, and which are not harmful for the membrane. In certain cases, PFCs may also include $BF_3$, $COF_2$, $F_2$, HF, $SiF_4$, $WF_6$, $WOF_4$, as long as they are not harmful for certain types of membranes. Perfluorocompounds do not include chlorofluorocarbons, or compounds comprising two hydrogen substituents or more, since such compounds do not usually behave as PFCs vis a vis the membrane and are not useful in semiconductor manufacturing processes.

Membranes useful in the invention are preferably glassy membranes, such as polymer membranes made preferably from polyimides, polyamides, polyamide-imides, polyesters, polycarbonates, polysulfones, polyethersulfone, polyetherketone, alkyl substituted aromatic polyesters, blends of polyethersulfone, aromatic polyimides, aromatic polyamides, polyamides-imides, fluorinated aromatic polyimide, polyamide and polyamide-imides, glassy polymeric membranes such as disclosed in U.S. Ser. No. 08/247,125 filed May 20, 1994 (now U.S. Pat. No. 5,599,380) and incorporated herein by reference, cellulose acetates, and blends thereof copolymers thereof, substituted polymers (e.g. alkyl, aryl) thereof and the like.

Asymmetric membranes are prepared by the precipitation of polymer solutions in solvent-miscible nonsolvents. Such membranes are typified by a dense separating layer supported on an anisotropic substrate of a graded porosity and are generally prepared in one step. Examples of such membranes and their methods of manufacture are disclosed in U.S. Pat. Nos. 4,113,628; 4,378,324; 4,460,526; 4,474,662; 4,485,056; 4,512,893, 5,085,676, and 4,717,394 all incorporated herein by reference. The '394 and '676 patents disclose preparation of asymmetric separation membranes from selected polyimides. Particularly preferred membranes are polyimide asymmetric gas separation membranes as disclosed in the '676 patent.

In a pressure driven gas membrane separation process, one side of the gas separation membrane is contacted with a complex multicomponent gas mixture and certain of the gases of the mixture permeate through the membrane faster than the other gases. Gas separation membranes thereby allow some gases to permeate through them while serving as a barrier to other gases in a relative sense. The relative gas permeation rate through the membrane is a property of the membrane material composition and its morphology. It has been suggested in the prior art that the intrinsic permeability of a polymer membrane is a combination of gas diffusion through the membrane, controlled in part by the packing and molecular free volume of the material, and gas solubility within the material. Selectivity is the ratio of the permeability's of two gases being separated by a material. It is also highly desirable to form defect-free dense separating layers in order to retain high gas selectivity.

Composite gas separation membranes typically have a dense separating layer on a preformed microporous substrate. The separating layer and the substrate are usually different in composition. Composite gas separation membranes have evolved to a structure of an ultrathin, dense separating layer supported on an anisotropic, microporous substrate. These composite membrane structures can be prepared by laminating a preformed ultrathin dense separating layer on top of a preformed anisotropic support membrane. Examples of such membranes and their methods of manufacture are disclosed in U.S. Pat. Nos. 4,664,669; 4,689,267; 4,741,829; 2,947,687; 2,953,502; 3,616,607; 4,714,481; 4,602,922; 2,970,106; 2,960,462; 4,713,292, 4,086,310; 4,132,824; 4,192,824; 4,155,793; and 4,156,597, all incorporated herein by reference.

Alternatively, composite gas separation membranes may be prepared by multistep fabrication processes, wherein first an anisotropic, porous substrate is formed, followed by contacting the substrate with a membrane-forming solution. Examples of such methods are described in U.S. Pat. Nos. 4,826,599; 3,648,845; and 3,508,994, all incorporated herein by reference.

U.S. Pat. No. 4,756,932 describes how composite hollow-fiber membranes may also be prepared by co-extrusion of multiple polymer solution layers, followed by precipitation in a solvent-miscible nonsolvent.

According to one embodiment of the present invention, the membrane can be post-treated with, or coated by, or coextruded with, a fluorinated or perfluorinated polymer layer in order to increase its ability to withstand harmful constituents in the gas mixture from which PFCs are to be separated, at low levels or temporary contact with such components.

The hollow-fiber spinning process depends on many variables which may affect the morphology and properties of the hollow-fiber membrane. These variables include the composition of the polymer solution employed to form the fiber, the composition of fluid injected into the bore of the hollow-fiber extrudate during spinning, the temperature of the spinneret, the coagulation medium employed to treat the hollow-fiber extrudate, the temperature of the coagulation medium, the rapidity of coagulation of the polymer, the rate of extrusion of the fiber, takeup speed of the fiber onto the takeup roll, and the like.

The gas mixture containing PFCs to be separated usually comprises at least one PFC and at least one carrier gas such as air, nitrogen, argon, helium, or the like and mixtures thereof.

In Table I are listed the most usual PFCs and other gases from waste streams from a semiconductor manufacturing process (not all of those gases are necessarily present—only some of them may be present in the exhaust).

The most common PFCs are usually the following ones:
for chamber cleaning: carbon tetrafluoride ($CF_4$), hexafluoroethane ($C_2F_6$), nitrogen trifluoride ($NF_3$), perfluoropropane ($C_3F_8$), sulfur hexafluoride ($SF_6$), trifluoromethane ($CHF_3$);

for the etching steps, the same PFCs are usually used but with several other gases such as argon, boron trichloride, chlorine, hydrogen bromide, hydrogen chloride, hydrogen fluoride, phosphine, silane, silicon tetrachloride, and the like.

Some of these gases are sometimes harmful for the membrane (as indicated in Table I), and it is preferred to remove them or destroy them from the feed gas mixture sent to the membrane. Usually it is preferred to remove the following compounds prior to sending the flow to the membrane: $WF_6$, HF, $F_2$, $NH_3$, $Cl_2$, HBr, HCl, $O_3$, and any silicon hydrides, germanium hydrides, and the like. To do this, various methods can be used such as using scrubber means (dry or wet scrubbers), thermal decomposition, plasma destruction, catalytic removal, and the like, to reach a level usually below about 1% vol. of said harmful substance in the feed. However, it is preferred to reach a level for each harmful substance lower than 10 ppm, most preferably lower than 1 ppm. It is also possible to treat the separated PFC non-permeate stream using one or more of those methods, referred to herein as post-treatment.

TABLE I

| Symbol | Name | Harmful to membrane |
|---|---|---|
| PFCs | | |
| $C_2F_6$ | Hexafluoroethane | not harmful |
| $CF_4$ | Tetrafluoromethane | not harmful |
| $CHF_3$ | Trifluoromethane | not harmful |
| $NF_3$ | Nitrogen trifluoride | not harmful |
| $SF_6$ | Sulfur hexafluoride | not harmful |
| $C_3F_8$ | Perfluoropropane | not harmful |
| $COF_2$ | Carbonyl fluoride | not harmful |
| Other gases (carrier gases, etc.) | | |
| Ar | Argon | not harmful |
| $AsH_3$ | Arsine | not harmful |
| $BCl_3$ | Boron trichloride | not harmful |
| $BF_3$ | Boron trifluoride | not harmful |
| $CH_3OH$ | Methanol | not harmful |
| Cl2 | Chlorine | harmful above 1% |
| $F_2$ | Fluorine | harmful above 1% |
| $H_2$ | Hydrogen | not harmful |
| HBr | Hydrogen bromide | harmful above 1% |
| HCl | Hydrogen chloride | harmful above 1% |
| HF | Hydrogen fluoride | harmful above 1% |
| He | Helium | not harmful |
| $N_2$ | Nitrogen | not harmful |
| $N_2O$ | Nitrous oxide | not harmful |
| $NH_3$ | Ammonia | harmful above 1% |
| NO | Nitric oxide | not harmful |
| $O_2$ | Oxygen | not harmful |
| $O_3$ | Ozone | harmful above 1% |
| $Si(OC_2H_5)_4$ | Tetraethyl Orthosilicate (TEOS) | not harmful |
| $PH_3$ | Phosphine | not harmful |
| $SiF_4$ | Silicon tetrafluoride | not harmful |
| $SiH_4$ | Silane | harmful above 1% |
| $WF_6$ | Tungsten hexafluoride | harmful above 1% |
| $WOF_4$ | Tungsten tetrafluoride oxide | not harmful |

$SiF_4$, $WF_6$, $WOF_4$, HF, $F_2$ while being perfluorinated compounds are usually not considered as PFCs.

The scrubber means to remove the harmful product for the membrane can be a dry scrubber (which usually removes at least $F_2$, HF, HCl, HBr, $Cl_2$, $NH_3$, $WF_6$ and $SiH_4$). Dry scrubbers are usually resin-type scrubbers, or soda-lime, while, some dry scrubbers comprising catalysts like $MnO_2$ can also remove ozone. Also, gaseous hydrides may be removed according to the methods disclosed in U.S. Pat. Nos. 4,743,435; 4,784,837; 4,910,001; 4,996,030, 5,182,088 and 5,378,439 incorporated herein by reference. When different scrubbers have to be installed in order to remove the various harmful constituents, it is preferred to install first the dry scrubber (or scrubbers) and then the wet scrubber. Upstream before the scrubbers, filters to remove particles from the stream are usually necessary (removal of particles having a diameter larger than 20 microns) and it is recommended according to the invention to provide a filter upstream having a pore size diameter less than 20 micrometers and preferably less than 10 micrometers, which removes particles and liquid droplets to avoid plugging of the membrane.

A wet scrubber is, for example, disclosed in the brochure entitled "Selecting a CDO™ for your Particular Application" from DELATECH Corporation, which brochure is incorporated herein by reference.

According to a preferred aspect of the invention, there exist some relationship between the pressure drop across the membrane (i.e. ΔP between the feed and the permeate), the temperature of the feed (i.e. the temperature of the membrane after temperature equilibration between the feed flow and the membrane itself) and the feed flowrate. It has been discovered that, for a certain constant flowrate of the feed gas on the membrane and temperature of the feed gas, when the pressure differential across the membrane increases, the recovery of PFCs like e.g. $C_2F_6$, decreases on the non-permeate or "residue" side of the membrane while this PFCs concentration increases on the permeate side of the membrane. Accordingly, it is preferred, according to the invention, to have a pressure drop ΔP across the membrane which is not high, usually smaller than about 13,600 kPa (2000 psig), preferably ranging from about 120 to about 1450 kPa (from about 3 to about 200 psig) and most preferably from about 240 and to about 510 kPa (from about 20 and to about 60 psig).

As far as the feed gas mixture is usually obtained at substantially atmospheric pressure, there is either the option to compress this feed to have a sufficient pressure drop across the membrane (but this is not preferred because usually, many of the species present in the feed may deteriorate the compressor) or create on the permeate side of the membrane a pressure lower than atmospheric pressure (which may be preferred because most of the species which may harm the vacuum means are retained on the non-permeate side of the membrane). To create this lowered pressure on the permeate side of the membrane, a vacuum pump or any other suction means is usually adequate. Alternatively, if the feed stream to the membrane is to be compressed, compression is preferably carried out after the feed stream has been pretreated using wet or dry scrubbers, filters, catalytic removal, pulsed corona destruction, thermal decomposition, and/or plasma decomposition, as explained in copending application Ser. No. 08/663,884, filed Jun. 14, 1996 incorporated herein by reference. Preferred compressors are sealed and oil-free, such as the compressors known under the trade designation POWEREX available from the Powerex Harrison Company, of Ohio, USA. Compression ratio (defined as the ratio of pressure at the compressor outlet divided by the pressure at the compressor inlet) of the compressor which feeds the membrane unit (or the first membrane unit of a series of membrane units) generally ranges from about 2:1 to about 10:1, it being appreciated that supplemental compression may be required at other membrane feed locations in a series of membrane units. It may be necessary to provide heat exchange between the compressed feed stream and a coolant, such as liquid nitrogen, for example if the temperature and/or pressure of the feed flowing into a particular membrane is to be controlled, or the PFC concentration in the non-permeate stream is controlled at a set-point value, as disclosed herein.

Whatever pressure drop across the membrane is chosen, according to the disclosure given hereabove, it is preferred to have a higher feed flow than a lower feed flow (even if such a system can work with a variable flowrate of the feed): the highest the feed flow, the highest the recovery. This feed flow can vary from near zero to about $10^5$ Nm$^3$/h per square meter of membrane available for separation, preferably from about $10^{-4}$ to about 10 Nm$^3$/h-m$^2$ and more preferably from about 0.1 to about 0.5 Nm$^3$/h-m$^2$.

Alternatively, the compressor may be positioned after the pretreatment means (dry and/or wet scrubbers, filters, and the like).

The temperature of the feed flow and/or the membrane shall also have an influence on the recovery of PFCs on the non-permeate side of the membrane. Usually, when the feed and/or the membrane temperature increases, then for a constant flowrate and pressure drop, the species of the gas mixture tend to permeate more through the membrane, particularly those which already permeate faster at lower temperature. For example, nitrogen and oxygen (air) which permeate much faster through the membrane than the PFCs at ambient temperature will permeate even much faster through the membrane at higher temperature, e.g. 50° C. to 60° C.

Usually, the temperature of the feed and/or the membrane can vary from about –10° C. to about 100° C., preferably from about 10° C. to about 80° C., and particularly preferably ranging from ambient temperature (usually about 20° C. to 25° C.) to about 60° C.

Another preferred method of operating the membrane separation units of the process and system of the invention is by operating each membrane unit to have a constant, set-point concentration of one or more PFC gases in the non-permeate stream exiting one or more of the membrane units. Some of the advantages of operating the process and system of the invention in this manner are that feed pressure fluctuations can be smoothed, and that the life of the membrane can be prolonged significantly. One way of maintaining the set-point concentration of the PFC in the non-permeate stream is to pass a portion of the non-permeate stream, preferably countercurrently, by the external side of the hollow fiber membrane (that is, on the permeate side of the hollow fibers of the membrane unit). This practice is more fully described in U.S. Pat. Nos. 5,240,471 and 5,383,957, both assigned to L'Air Liquide S.A., with the exception that the patents do not describe separation of PFCs using these techniques. Both of these patents are incorporated herein by reference for their teaching of sweep gas techniques. Thus, a portion or all of a non-permeate stream of stage N can be used as feed stream for stage N+1 and/or N+2, etc., bearing in mind that there is usually, in practice, a small pressure drop between stage N, stage N+1 and stage N+2, etc. This means that the pressure on the non-permeate (feed side) of stage N is greater than the pressure on the feed side of any subsequent stage, such as N+1 or stage N+2.

After this first concentration step with one or a plurality of membranes, it is preferred to then carry out a second step wherein the various PFCs are at least partially separated from each other, or more abundant PFCs separated from minor amounts of other PFCs. Different separation techniques for separating two or more perfluorocompounds can be used such as distillation, adsorption, condensation, and the like. Preferably, and because it may be more appropriate for the streams which are coming out of a semiconductor manufacturing tool, a condensation process can be used such as the one known under the tradename SOLVAL of Air Liquide America Corporation disclosed in the Technical Bulletin entitled "Solval™ Solvent Condensation and Recovery System", 1994, and incorporated herein by reference. Basically, in this condensation process, the effluent from the non-permeate side of one or a plurality of membranes is fed into a heat exchanger. Liquid nitrogen or another cooling medium is introduced into the heat exchanger and flows through the cooling coils. The mixture of PFC with $N_2$ is introduced into the shell of the heat exchanger and flows around the coils as it passes through the shell. The mixture is cooled and part of the PFC vapors are coalesced, liquefied and collected based upon the temperature at the cooling coils. The higher the liquid nitrogen flowrate into the exchanger, the lower the temperature at the cooling coils, and therefore, more of PFCs will be liquefied.

In some preferred embodiments, the PFC mixture after concentration comprises species whose boiling points are close and it is therefore difficult to separate them by fractional condensation. For example, $C_2F_6$ has a normal boiling point of –78.2° C. and $CHF_3$ has a normal boiling point of –82.1° C.; $CF_4$ has a normal boiling point of –127.9° C. and $NF_3$ has a normal boiling point of –129° C. When it is desired to separate a mixture comprising at least two species having close boiling points, then a first separation by, for example, condensation is made between the various species having boiling points not too close from each other in order to provide substantially pure species or a mixture of species having close boiling points. Then, the mixture of species having close boiling points are separated by another process, for example, adsorption when one of the species of the mixture is more polar than the other. $NF_3$ and $CF_4$ may be separated using molecular sieves (such as NaX, CaX and NaA, wherein the "A" designates 5 Angstrom cage size, and the "X" designates a 10 Angstrom cage size); activated carbon; or the like, wherein the polar species (such as $NF_3$ and $CHF_3$) are preferentially adsorbed, as opposed to non-polar species such as $CF_4$.

FIG. 1 illustrates the efficacy of a burner to destroy PFCs versus temperature (° C.) in a prior art process. For example, when an air-fuel burner is used, the temperature of the flame which is reached, if almost 100% of $NF_3$, $CCl_2F_2$ (which is not a PFC but is chlorofluorocompound used by the electronic industry), $CHF_3$ and $SF_6$ are destroyed (generating HF and other undesirable species), $C_2F_6$ and $CF_4$ are only partially destroyed, particularly $C_2F_6$ which is only 50% destroyed: the combustion gases cannot accordingly be vented. However, when using an oxy-fuel flame which temperature is about 1400° C., it is possible to destroy most of the $C_2F_6$, while still generating undesirable species. In the present invention, combustion at 900° C. may remove all PFCs but $C_2F_6$ and $CF_4$, which can then be recycled together.

Figure 2:
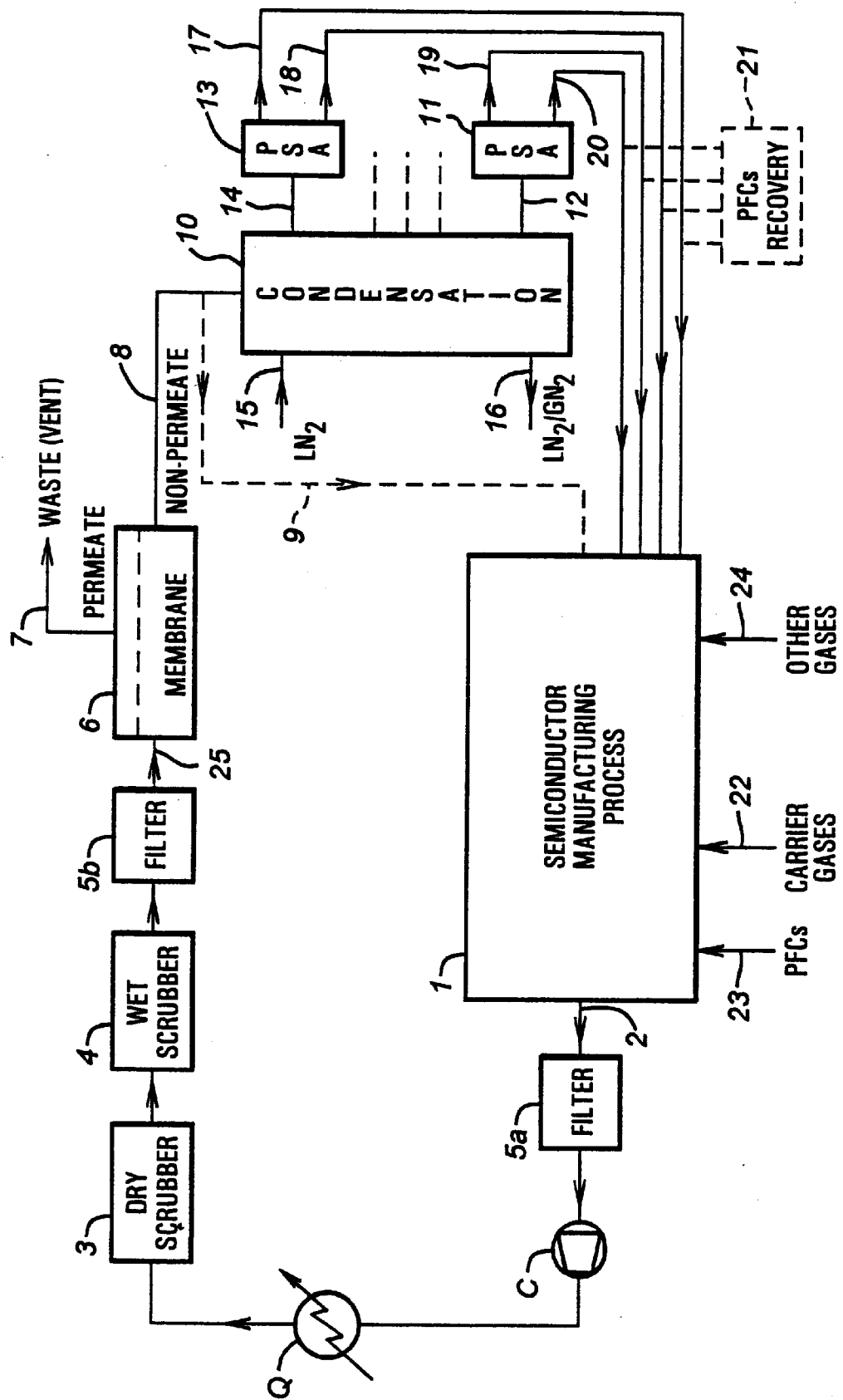
FIG. 2 represents a schematic drawing of one process and system according to the invention.

The general features of one process according to the invention are illustrated in FIG. 2, wherein a semiconductor manufacturing process is represented by the reference numeral 1 (which may be any type of process using PFCs and rejecting PFCs). The PFCs and carrier gases fed to process 1 are represented by 23 and 22, respectively (bulk and/or cylinder delivery through traditional bulk systems or gas cabinets well known in the electronic industry).

A waste gas mixture of PFCs, carrier gases and any other gases 24 (such as chemically reactive gases) is recovered from process 1 in an exhaust line 2. The waste gas mixture is preferably passed through filter 5a, and then compressed in a compressor C. The compressed gas mixture is then optionally routed to a cooler or heater Q to provide a desired temperature for the compressed gas mixture. The gas mixture is then preferably scrubbed in a dry scrubber 3 to remove most of silicon hydrides, $NH_3$, $AsH_3$, tetraethyl orthosilicate (TEOS), halogen, halides, then preferably scrubbed in a wet scrubber 4 to remove most of hydrides, halides, halogen gases (according to the nature of the gas mixture provided in 2, only dry scrubber 3 or wet scrubber 4 may be necessary), then filtered in a filter 5b to remove dust, particles, droplets, and the like, having size greater than 20 micrometers. Additionally, particles and dust may be removed in a filter upstream from dry scrubber 3. A gas mixture in 25 no longer contains any substantial amount of harmful component for a membrane unit 6. Gas stream is sent on the feed side (bore side) of a plurality of hollow fibers of membrane unit 6, the carrier gases of the mixture then permeate through the hollow fibers of membrane unit 6 and are recovered or vented as a waste gas 7 (it for example, the carrier gas comprises helium, and also argon, it may be useful to recover it and recycle it in the process, with further purification or not). The non-permeate stream which comprises the PFCs (concentrated) are recovered in 8 and either directly recycled to process 1 (or stored in bulk to be later reused in process 1) through a line 9 or sent to a separation unit, for example a condensation unit 10. In condensation unit 10, a heat exchanger receives liquid nitrogen $LN_2$ in line of $LN_2/GN_2$ in line 16, which condenses the high boiling point species (by using different flowrates of $LN_2$, one can easily control the condensation of various products) which are recovered as a liquid on line 12 and sent to, for example, to an adsorption process 11 which separates the polar fraction from the non-polar fraction (respectively 19, 20), which fractions are either recovered in 21 for further treatment on-site or off-site (the dotted lines indicate that this is not the preferred alternative) or recycled/stored in process 1.

The gaseous fraction is sent through line 14, for example a pressure swing adsorption system 13 (or any other adsorption system) wherein the adsorbed species (one or several) are recovered on line 17 and wherein the non-adsorbed species (one or several) are recovered on line 18. Both products on lines 17 and 18 are either recovered in 21 (for example off-site treatment) or recycled in process 1.

Those species or mixture of species are either recycled in process 1 or recovered in the PFC recovery unit 21. At 24 are the other gas inlets in the process (for example chemical gases other than PFCs and other than carrier gases used to dilute the other gases or to purge a chamber). Those other gases are sometimes those which are harmful for the membrane (for example $SiH_4$, $WF_6$, and the like) and which are used in other steps of the manufacturing process of a semiconductor.

Figure 3:
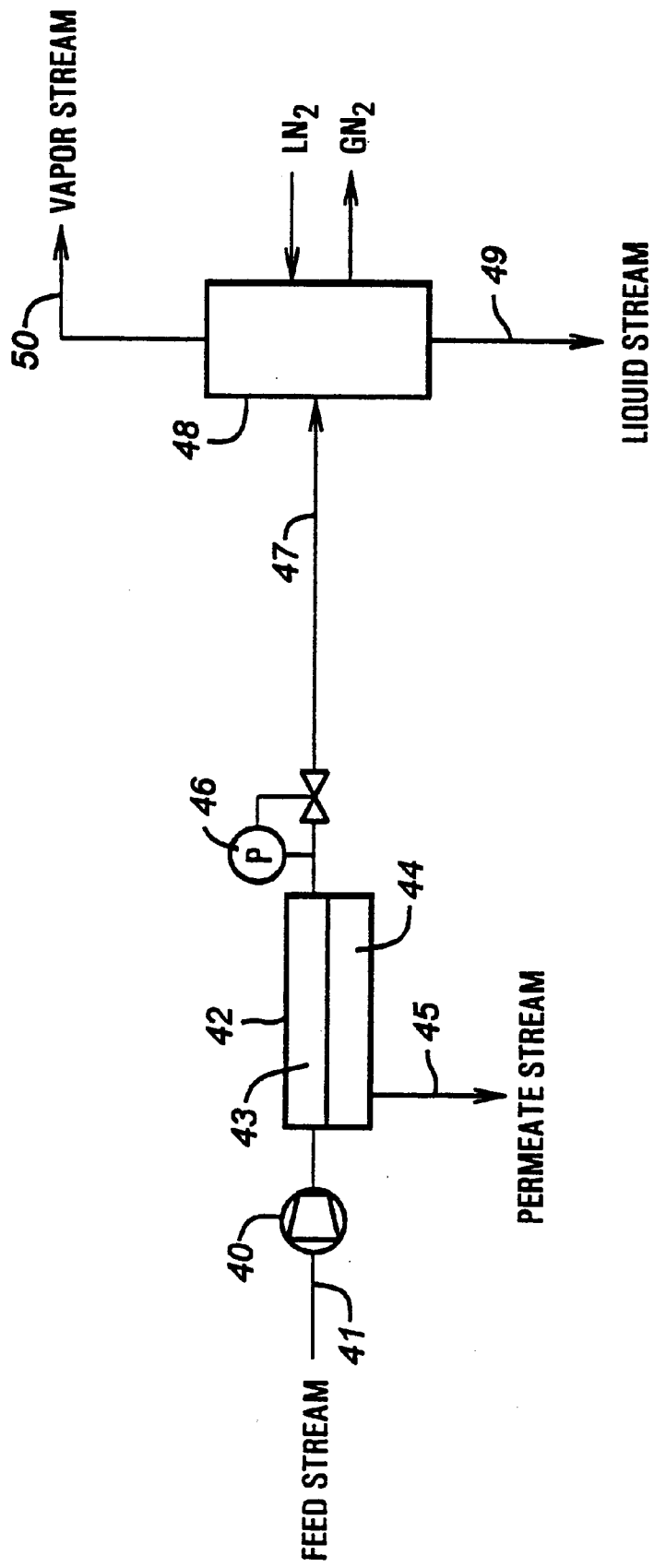
FIG. 3 is a detailed view of a portion of the process and system of FIG. 2.

FIG. 3 is a detailed partial view of FIG. 2 of the membrane system and the condensation system. A feed stream 41 (wherein all harmful components have been removed) is compressed in compressor 40 and the stream is fed to the feed side 43 of membrane 42. The permeate stream 45 from the permeate side 44 of the membrane is usually vented. A pressure regulator 46 which may or may not be required controls the pressure downstream of the membrane (on the non-permeate stream), while the non-permeate stream 47 is fed, for example, to a condensation system 48, which separates by heat exchange with liquid nitrogen $LN_2$ the condensed stream or liquid stream 49 from the uncondensed stream or gaseous stream 50. After heat exchange, the liquid nitrogen $LN_2$ is substantially totally vaporized as gaseous nitrogen $GN_2$.

Figure 4:
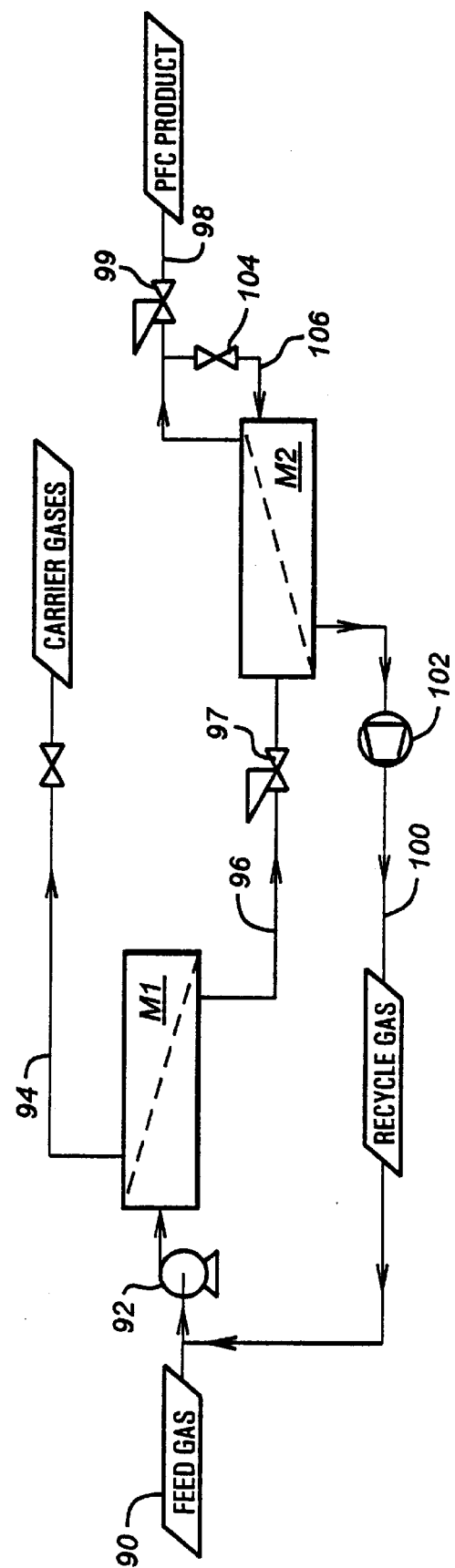
FIGS. 4–7 illustrate four different embodiments of the invention.

FIG. 4 represents a simplified schematic diagram of one process and system embodiment of the invention. Feed gas 90 from a semiconductor manufacturing process is compressed in a compressor 92 prior to entering a first stage membrane M1. First stage membrane M1 creates a permeate stream 94 comprised primarily of carrier and process gases, and a non-permeate stream 96, enriched in one or more PFCs. A back pressure regulator 97 provides a pressure drop across membrane M1. Non-permeate stream 96 then enters a second stage membrane M2, producing a second non-permeate PFC enriched stream 98, and a second stage permeate stream 100 comprised primarily of carrier and process gases which are impermeable to the M1 membrane but which are permeable to the M2 membrane. A second back pressure regulator 99 maintains a pressure drop across second stage membrane M2. Optionally, streams 94 and 100 may be combined and either disposed of; or recycled as shown for stream 100. Optional and preferred components of the system embodied in FIG. 4 include provision of a valve 104 and conduit 106 which allow a portion of the PFC product stream 98 to be swept across the permeate side of membrane M2, thereby affording process efficiencies as described in the '471 and '957 patents, previously incorporated by reference. Also, an optional vacuum pump is illustrated at 102 on the recycled gas stream. Vacuum pump 102, if present, allows recycled gas stream 100 to reenter the system with the feed gas.

Figure 5:
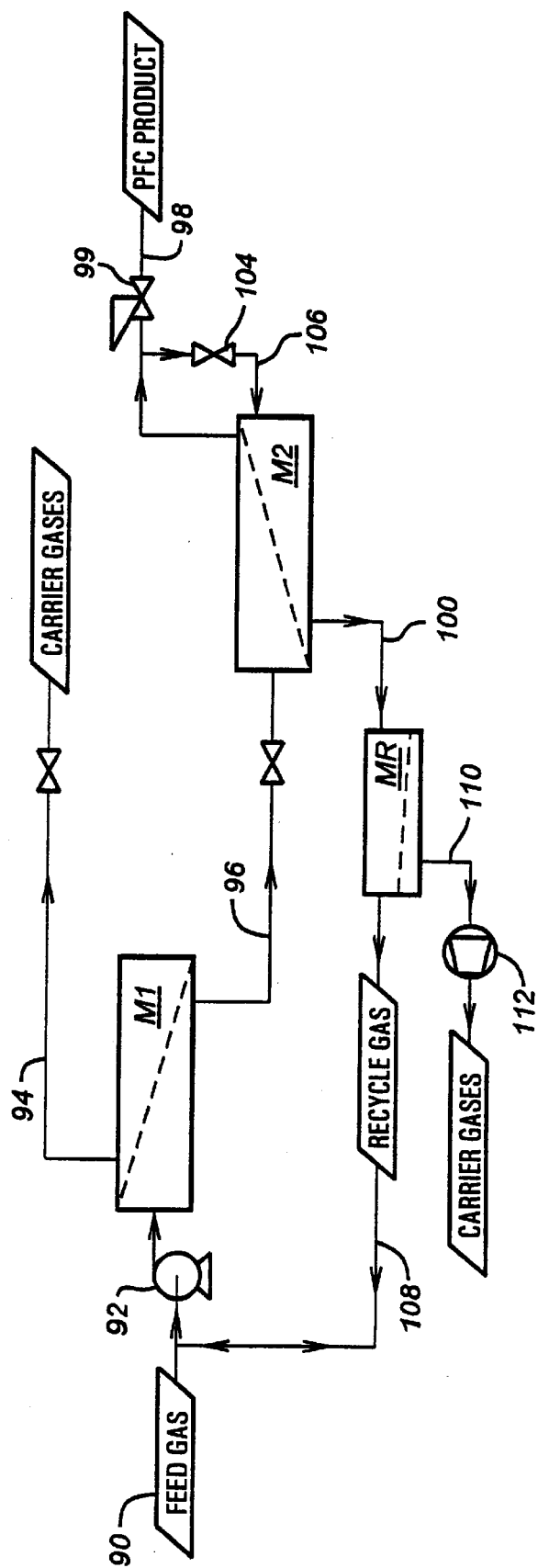

FIG. 5 illustrates a system and process substantially in accordance with that of FIG. 4, with the provision of a recycle membrane $M_R$ in recycle gas line 100. Also provided is a conduit 110 and vacuum pump 112 which allows separation via recycle membrane $M_R$ of carrier gases. Thus the recycle gases in conduit 108 are comprised primarily of other process gases as defined herein.

Figure 6:
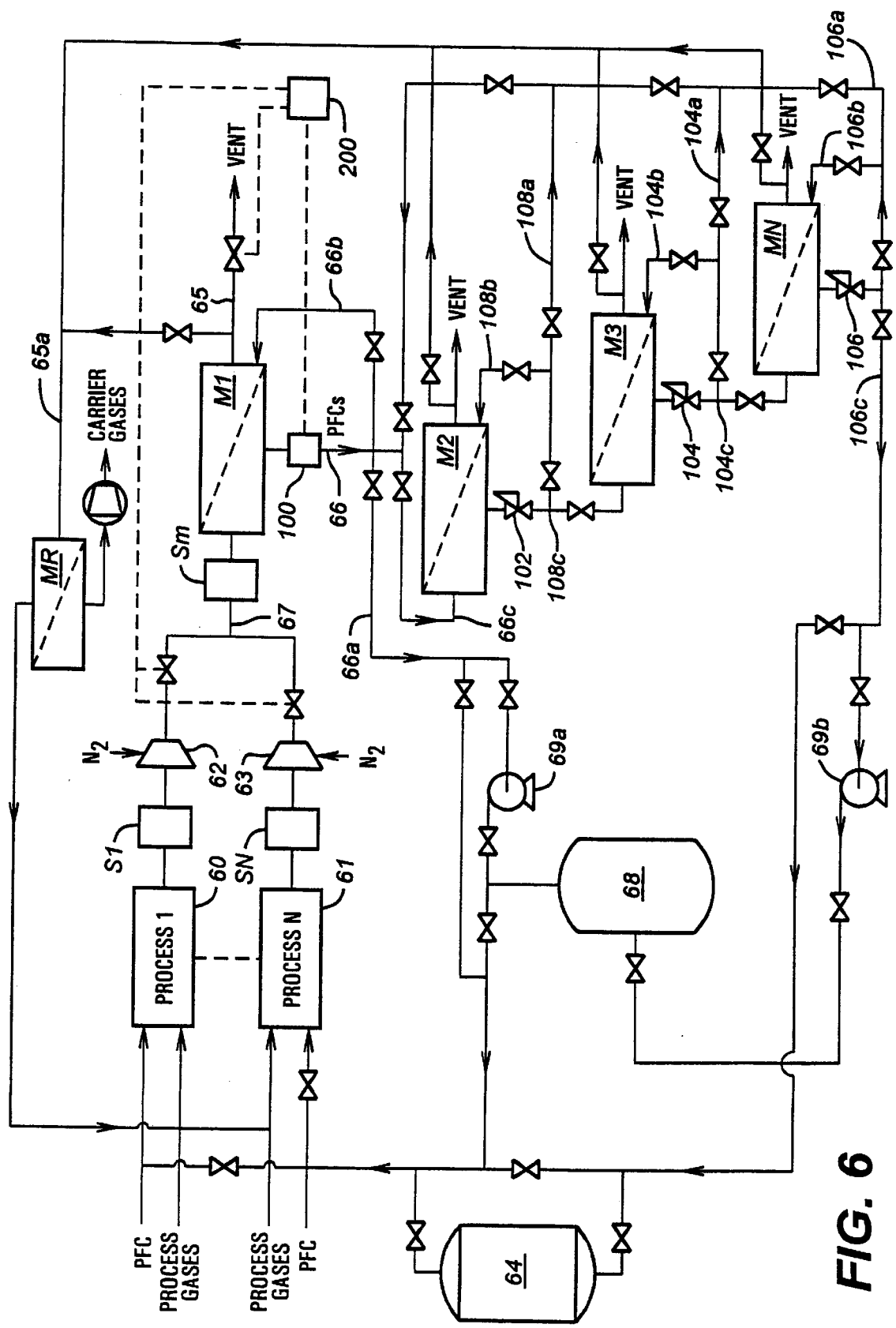
Figure 7:
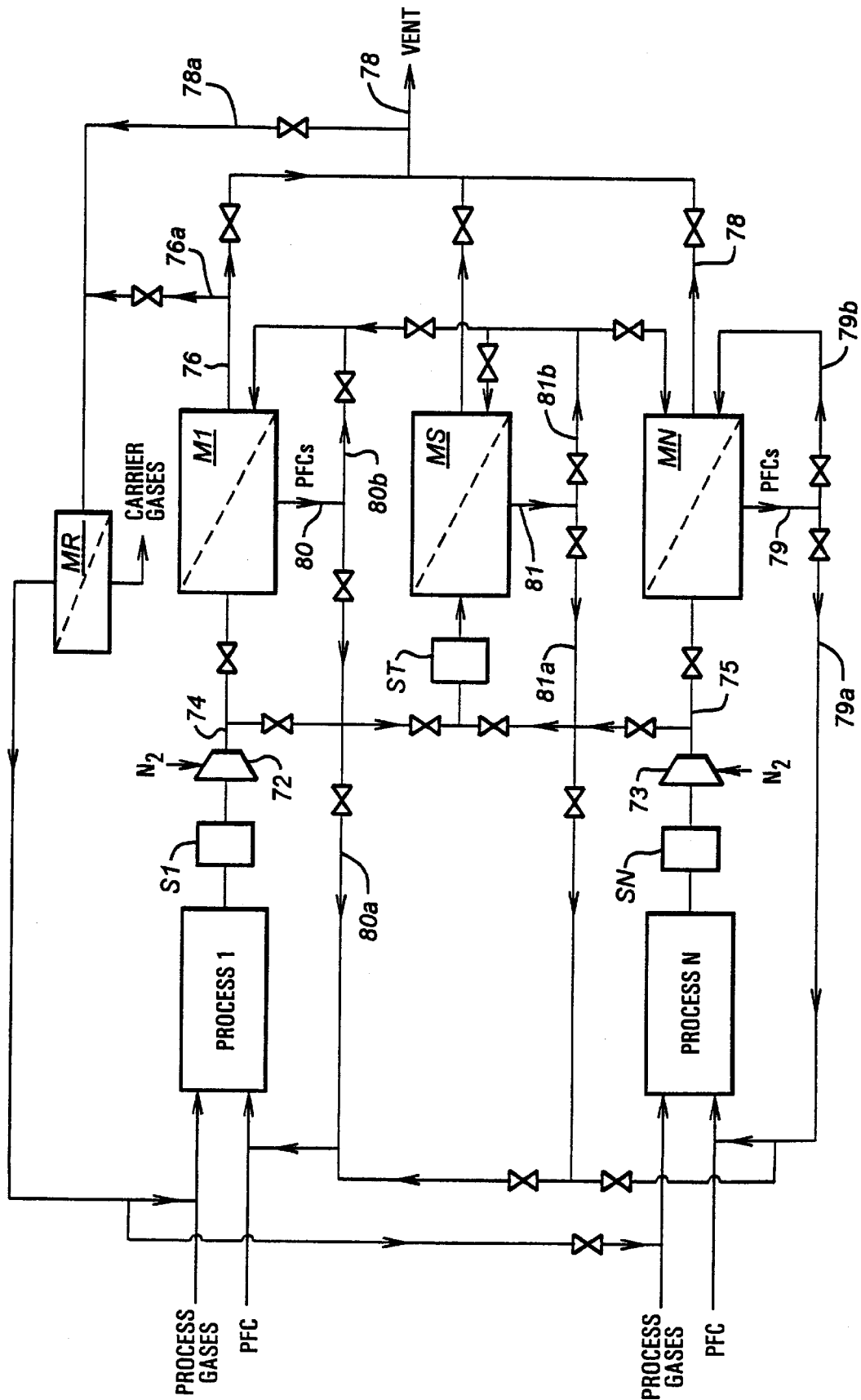

FIGS. 6 and 7 illustrate two other possible embodiments of the invention. In FIG. 6, several identical or different processes 60 . . . 61 are available for use (either simultaneously or not), using similar or different PFC gases and other gases designated as process gases. The gas exhausts from 60 . . . 61 are preferably scrubbed in scrubbers $S_1$, $S_N$, and then are preferably diluted with $N_2$, and compressed respectively in 62 . . . 63, and mixed together as a single stream 67 (in fact the various processes 1 . . . N may either successively or simultaneously discharge exhaust gases). Single stream 67 is then preferably filtered at $S_m$ as a final cleaning step, then fed to a membrane unit M1 of the invention wherein the permeate 65 may be vented or rcycled in line 65a to a recycle membrane $M_R$ which separates usable process gases from carrier gases non-permeate 66 and 66a (concentrated PFCs) may be recycled to one or several of the processes 1 . . . N, respectively 60 . . . 61. Alternatively, non-permeate stream 66c may be routed to one or more membrane units $M_2$, $M_3$, . . . $M_N$, thus improving the purity of the PFCs. Preferably, a sweep gas stream 66b may be employed to sweep the permeate side of M1. Membrane units $M_2$, $M_3$ and $M_N$ also may have sweep gas streams. Other preferred features of the invention include the provision of one or more vacuum pumps (69a and 69b), a high pressure PFC storage vessel 68, and/or a surge tank 64. As an example of multiple different processes, one process may be a metal oxide etch, another might be an oxide etch, and yet another might be a tungsten CVD process.

Further illustrated in FIG. 6 is a mass flow measurement device 100 on the non-permeate stream 66 of membrane unit $M_1$ which may be used to control the flow of the permeate stream indirectly via controller 200, which accepts a signal from flow measurement device 100 and adjusts flow control valves in conduits 67 and 65. Conduit 66 also preferably includes a backpressure regulator, which is not illustrated for clarity. Backpressure regulators 102, 104, and 106 serve the function as described above for backpressure regulator 97 (FIG. 4). Other process control schemes are certainly feasible. For example, it may be advantageous, as previously mentioned, to operate $M_1$ using a set point PFC concentration in the non-permeate stream 66. In such embodiments, the flow measurement device may also include analysis equipment to determine the PFC concentration in conduit 66. Similar process controls may be used for membrane units M1, M2, M3, and MN as desired. Also, similar piping arrangements may be employed in the latter membrane units, as denoted at 108a, 108b, 108c, 104a, 104b, 104c, 106a, 106b, and 106c.

FIG. 7 is a parallel processing embodiment wherein each process 1 ... N is associated (after dilution with nitrogen and compression respectively in 72 and 73) with a membrane system $M_1$ ... $M_N$, respectively, according to the invention. Each feed stream 74 ... 75 is fed to a membrane system $M_1$ ... $M_N$ (with pretreatment systems $S_1$ ... $S_N$ if necessary). The permeate gases are vented together at 78 while each non-permeate 79, 80 is recycled, preferably to its corresponding process. Alternatively, rather than venting all of the permeate streams through vent line 78, permeate from one or more membranes, for example, membrane $M_1$, may be recycled through various conduits 76, 76a, and 78a, as illustarted in FIG. 7. Furthermore, non-permeate streams 79, 80, and 81 may be recycled to their corresponding process through lines 79a, 80a, and 81a, respectively. Some non-permeate streams may be used as sweep gases on the permeate side of each membrane. The sweep gases are preferably provided through lines 80b, 81b, and 79b, for membranes $M_l$, $M_s$, $M_n$, respectively. Preferred systems of the invention include a redundant membrane unit $M_s$, preferably having its own pretreatment unit $S_T$. Also preferred is a recycle membrane unit $M_R$, which separates usable reactive process gases from carrier gases. Note that with suitable arrangement of valves, this embodiment can operate in parallel or series (cascade) mode.

It is important to note that for all these different embodiments of the invention, it may in some instances be preferred to create a pressure drop across the membrane. In one embodiment this may be done by creating vacuum on the permeate side of the membrane while keeping the feed gas at about atmospheric pressure, which is usually about the pressure of the gas mixture released from the semiconductor manufacturing process. As long as usually only the carrier gases permeate through the membrane, those gases cannot damage a vacuum pump or other vacuum system, while on the contrary, compressing the gas mixture upstream from the membrane would not only mean compressing more gas, but it would also mean a risk for the compressor means.

Figure 8:
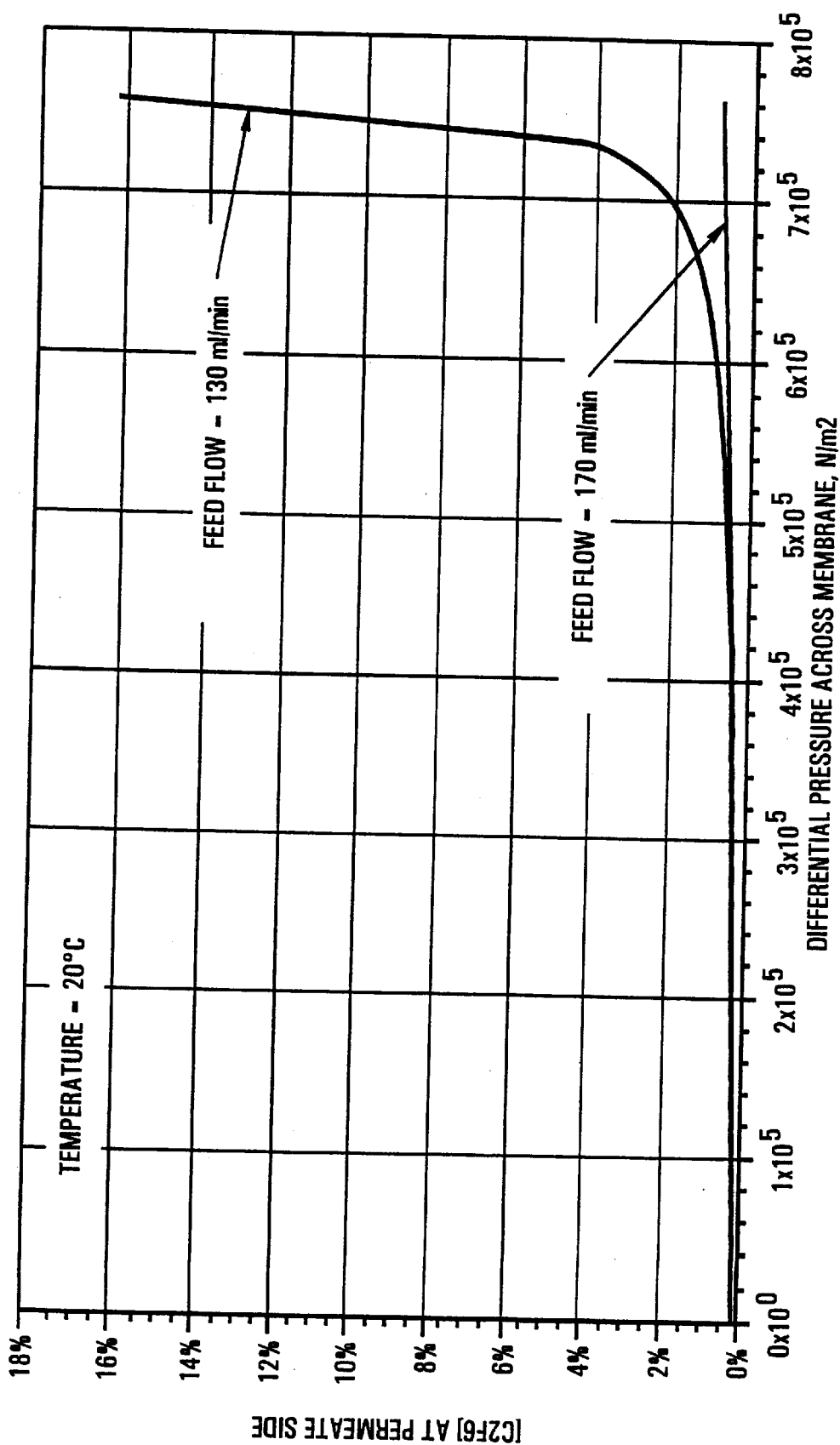
FIG. 8 illustrates PFC concentration on the residue side (permeate) of the membrane versus the pressure differential across the membrane, for different flowrates of the feed stream.

FIG. 8 illustrates at 20° C. for two different flowrates of the feed flow of 170 ml/min and 130 ml/min, respectively, on a hollow-fiber membrane made of polyimide having a surface of about 0.2 m² wherein the feed flow is sent into the hollow fiber with a permeation towards the outside hollow fiber. FIG. 8 clearly illustrates for low pressure drop between the non-permeate and the permeate sides of the membrane, no concentration of $C_2F_6$ occurs (0.2% of $C_2F_6$ recovered on the non-permeate side with the "residue"). For higher pressure drops, depending on the feed flow, the concentration of $C_2F_6$ then increases with an onset point of about $7\times10^5$ N/m² ($\Delta P$ across the membrane) for a feed flow of 130 ml/min. For higher flowrates (170 ml/min) the onset point is obviously higher (increases with feed flow).

Figure 9:
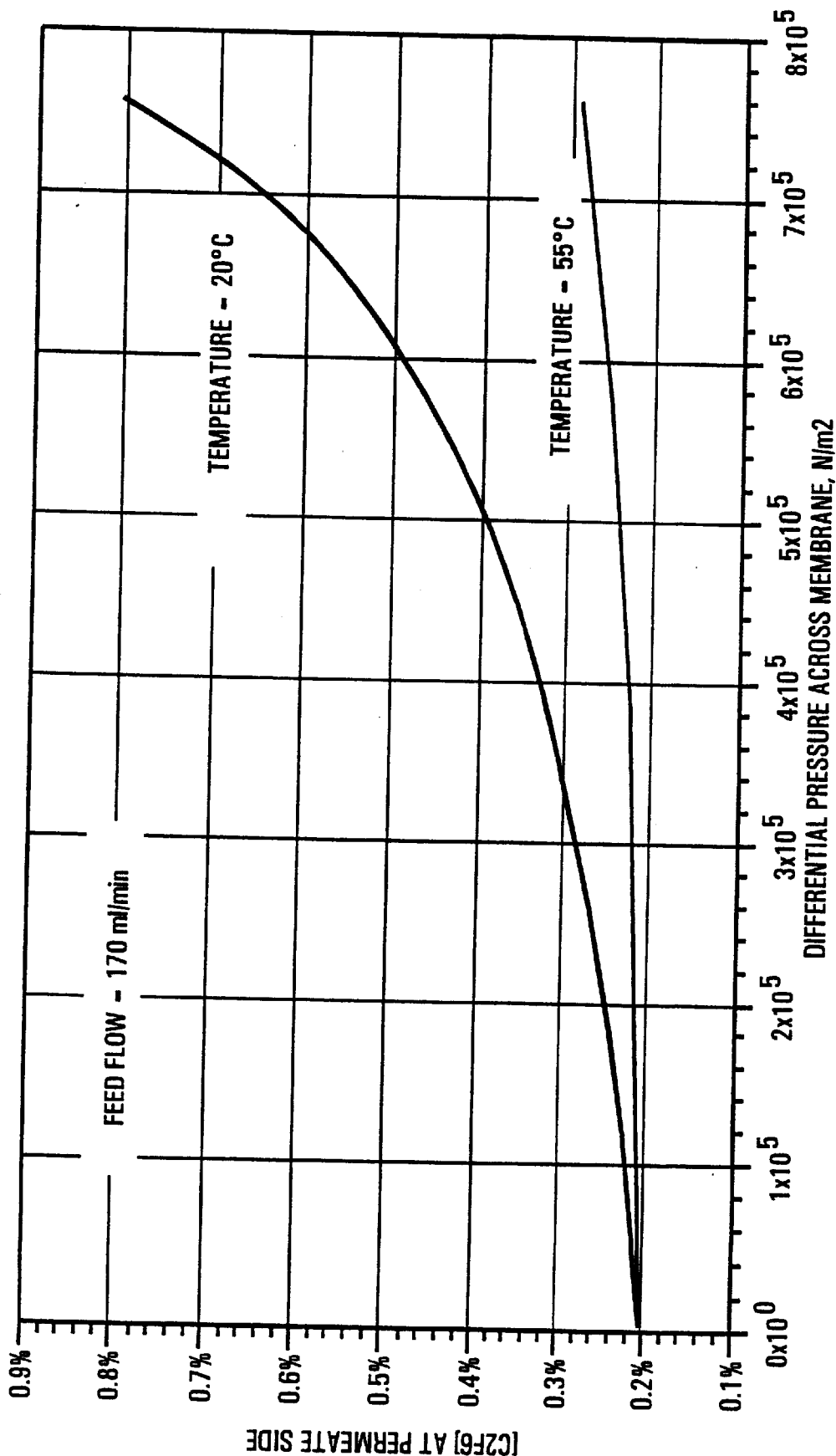
FIG. 9 illustrates PFC concentration on the residue side (permeate) of the membrane versus the pressure differential across the membrane, for different temperatures of the feed flow.

FIG. 9 illustrates the effect of the temperature of the feed flow (or of the membrane)—same membrane as used for FIG. 8. For a higher temperature of the flow, a higher differential pressure across the membrane is needed to achieve the same concentration of PFCs.

Figure 10:
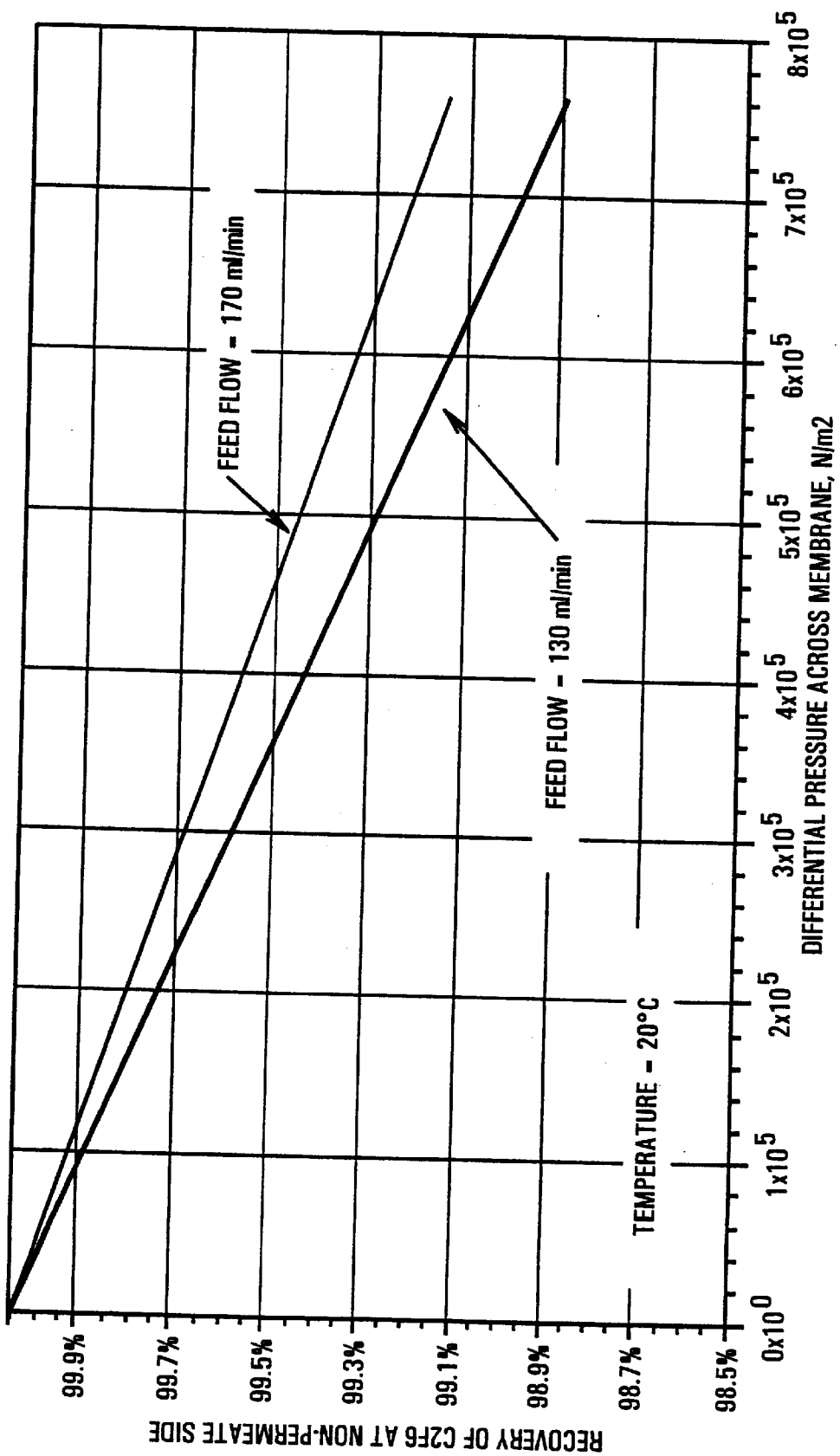
FIG. 10 illustrates PFC concentration on the recovery side (non-permeate side) of the membrane versus the pressure differential across the membrane, for different flowrates of the feed stream.

FIG. 10 illustrates the recovery rate of $C_2F_6$ on the non-permeate side of the membrane versus the differential pressure across the membrane for two different flowrates: for very low differential pressure, about all of the $C_2F_6$ is recovered while the rate of $C_2F_6$ permeating through the membrane progressively increases with the pressure drop across the membrane, such rate increasing faster for lower flowrates (compare curves for 130 ml/min. and 170 ml/min).

Figure 11:
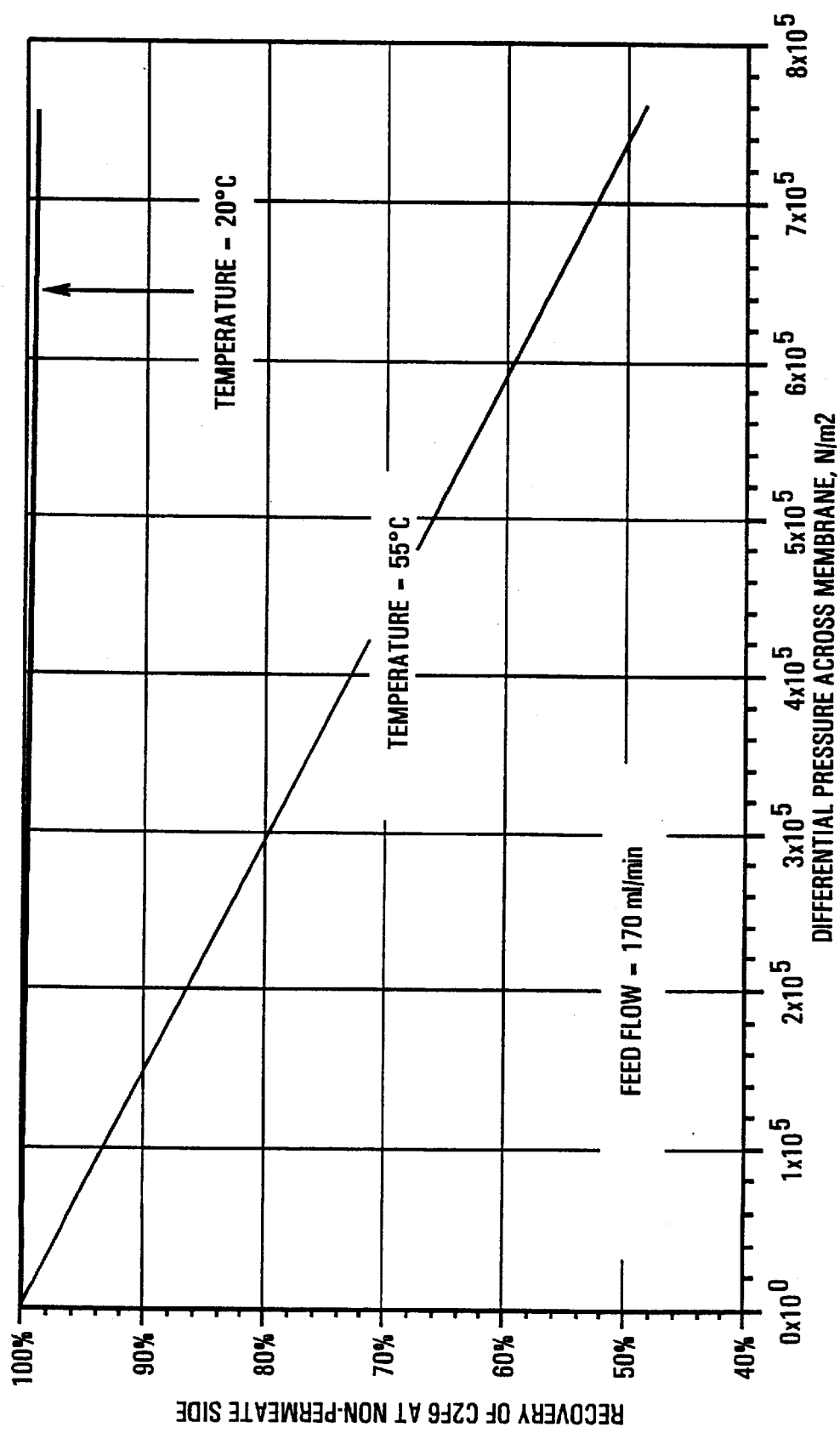
FIG. 11 illustrates PFC concentration on the recovery side (non-permeate side) of the membrane versus the pressure differential across the membrane, for different temperatures of the feed flow.

FIG. 11 illustrates the effect of temperature for a flow of 170 ml/min.: while only an extremely low amount of $C_2F_6$ permeates at 20° C., almost half of it permeates at 55° C. for a pressure drop of about $7\times10^5$ N/m².

From a recovery standpoint (FIGS. 10 and 11), it is thus better to operate at high flowrates and ambient temperature for a given pressure drop. But FIGS. 8 and 9 indicate that a substantial pressure drop is necessary to have a certain purity of $C_2F_6$ (and thus a certain concentration).

Figure 13:
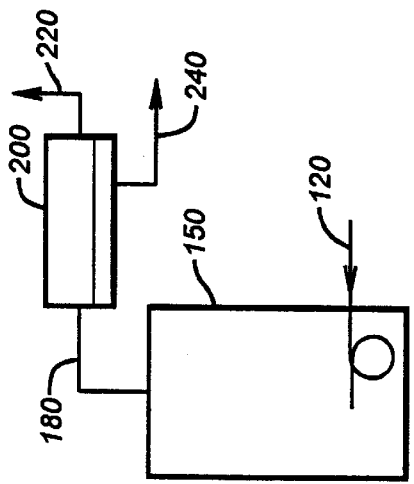
FIG. 13 illustrates schematically a gas cabinet including a membrane recovery unit.
Figure 14:
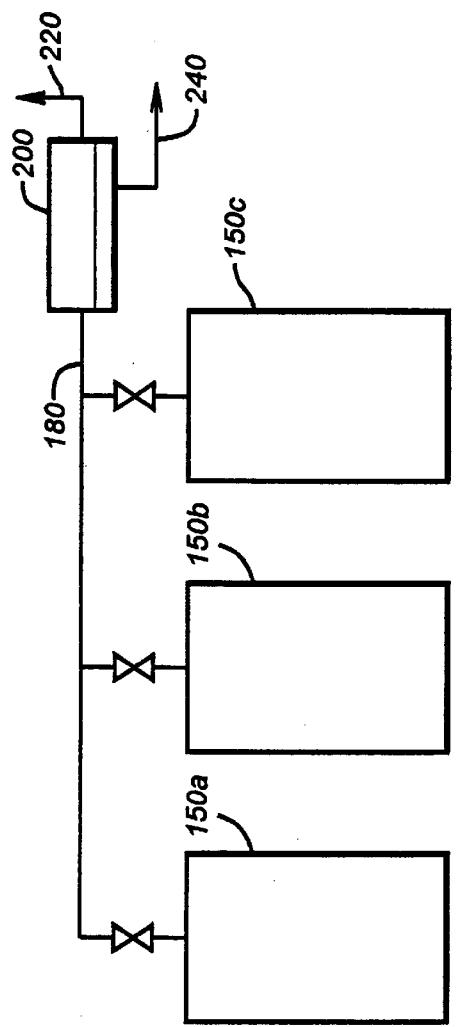
FIG. 14 illustrates multiple gas cabinets venting into a common membrane recovery unit.
Figure 12:
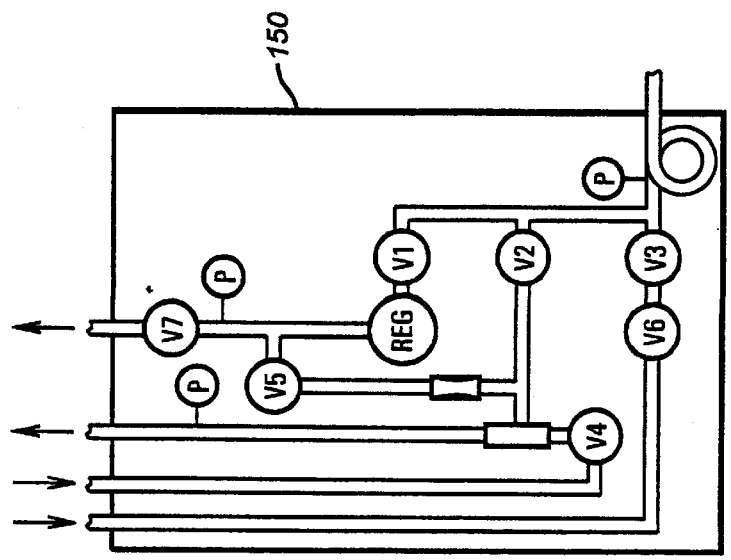
FIG. 12 illustrates schematically a prior art gas cabinet.

FIGS. 12–14 illustrate another aspect of the invention. Gas cabinets (sometimes known as gas panels; are well known in the semiconductor manufacturing art and need little explanation to the skilled artisan. A gas cabinet 150 for PFCs will have a PFC vent stream. PFC vents from tube trailers, clean rooms, gas packaging facilities, and the like, also need little explanation. Although the following discussion is for gas cabinet vents, the idea pertains to the recovery of a relatively pure PFC stream from any venting of PFCs.

All automated cabinets employ specific purging routines before and after cylinder change. The pre-purge routine generally is utilized to purge process gas while a post-purge routine is generally used to remove purging intrusions. The following describes different operational modes of a typical gas cabinet. See FIG. 12.

Process Gas Delivery Mode

Process gas flows first through V1, then through a pressure reducing regulator and then through V7. Valves V2, V3 and V5 are bypassed during the process gas delivery mode.

Pre-Purge Routine

Vent Purge

Once the process gas cylinder valve has been closed, the vacuum generator is activated with nitrogen by V4 and the vent line is purged for atmospheric removal. The vent area between V2 and V5 is also evacuated at this time. V4 is then cycled on and off to back fill the area between V2 and V5 with nitrogen.

Vent Mode

With V7 closed and V4 on, the process gas is vented through V5 and V1 remains open until the process gas safely reaches atmospheric pressure (sensed by a pressure transducer p). A 0.040 inch orifice is located on the vacuum inlet of the vacuum generator to restrict the venting flow rate.

Vacuum Mode

With V4 on, V1 closed and V2 opened, a vacuum of 22–24 inches Hg is generated between V1 and the cylinder valve. Note: V1 is always closed during the purging routine.

Nitrogen Pressure Mode

With V4 on, V2 and V3 opened, V6 is opened allowing nitrogen pressure (80 psi) to overcome the vacuum and to pressurize the system with nitrogen between V1 and the cylinder valve. When V6 is closed, a vacuum is then again generated between V1 and the cylinder valve. V6 is cycled on and off multiple times in the pre-purge to create the vacuum/pressure purging action.

Nitrogen Purge Gas Bleed

Once pre-purge is complete, a pigtail purge bleed is activated by partially opening V6 while V3 is open. When the process gas cylinder is removed, a pre-set flow of nitrogen will flow from the pigtail preventing atmospheric intrusion.

Post Purge Routine

Vacuum Mode

With V4 on and V2 opened, a vacuum of 22–24 inches Hg is generated between V1 and the cylinder valve.

Nitrogen Pressure Mode

With V4 on, V2 and V3 opened, V6 is opened allowing nitrogen pressure (80 psi) to overcome the vacuum and to pressurize the system with nitrogen between V1 and the cylinder valve. When V6 is closed, a vacuum is then again generated between V1 and the cylinder valve. V6 is cycled on and off multiple times in the pre-purge to create the vacuum/pressure purging action. This sequence ends with the pigtail up to V1 under vacuum.

Process Gas Flush

The process gas cylinder valve is now opened. V4 is turned on and then V1 is opened. Next V5 is cycled on and off allowing process gas to be flushed through the vent through an orifice. Once this sequence is complete the system returns to the Process Gas Delivery Mode.

FIG. 13 illustrates schematically the provision of a pure PFC stream 120 to a gas cabinet 150 (the internals are not illustrated for clarity). Gas cabinet 150 has a vent tube or conduit 180 which leads to a membrane separator unit 200 having a non-permeate stream 220 and a permeate stream 240 as explained herein.

FIG. 14 illustrates schematically the provision of multiple (in this case three) gas cabinets 150a, 150b, and 150c, all venting into a common membrane recovery unit 200.

Various examples will now exemplify aspects of the invention.

EXAMPLES

Example 1

A feed stream comprising 0.95% vol. $C_2F_6$, 1.03% vol. $CHF_3$, 1.10% $CF_4$, and 96.93% nitrogen at a pressure of 544,218 Pascal, a temperature of 293K (20° C.) and a flowrate of 193 sl/m (standard liter per minute) is fed on the feed side of a polyimide membrane made according to U.S. Pat. No. 5,085,676. A vacuum system creates a low pressure on the other side of the membrane: the permeate stream recovered is at a pressure of 6,579 Pascal, a temperature of 293K and a flowrate of 181 sl/m, while on the non-permeate side, the pressure remains 544,218 Pascal, the temperature 293K and the flowrate 12 sl/m. The non-permeate (concentrated) stream from the membrane comprises:

$C_2F_6$ 15.66% vol.
$CHF_3$ 9.54% vol.
$CF_4$ 18.15% vol.
$N_2$ 56.65% vol.

The permeate stream from the membrane comprises:

$C_2F_6$ 0.02% vol.
$CHF_3$ 0.48% vol.
$CF_4$ 0.01% vol.
$N_2$ 99.49% vol.

The non-permeate stream is further sent to a cryogenic condensation system as disclosed hereabove wherein 0.4942 pound of liquid nitrogen per pound of non-permeate stream is contacted by heat exchange, thus condensing most of the PFCs as indicated hereafter. The compositions of the vapor and liquid streams are the following:

Vapor Stream:

$C_2F_6$ 1.03% vol.
$CHF_3$ 0.69% vol.
$CF_4$ 16.5% vol.
$N_2$ 81.78% vol.

This vapor stream comprises essentially $CF_4$ diluted in nitrogen.

Liquid Stream $C_2F_6$ 47.83% vol.
$CHF_3$ 29.00% vol.
$CF_4$ 21.81% vol.
$N_2$ 1.37% vol.

The liquid stream is essentially concentrated into three liquid species $C_2F_6$, $CHF_3$ and $CF_4$. The liquid stream is then either recycled into the process from where the feed flow was coming or recovered and shipped for further treatment (concentration, separation, etc.)

The vapor stream is preferably recycled to the input of the cryogenic condensation system or may be treated (for example scrubbed) and discarded.

Example 2

Under the same conditions as in Example 1, a feed stream comprising 0.95% vol. $C_2F_6$, 1.03% vol. $CHF_3$, 1.10% $CF_4$, and 96.93% nitrogen at a pressure of $5.44 \times 10^5$ Pascal, a temperature of 20° C. and a flowrate of 193 sl/m (standard liter per minute) is sent on the same membrane as in Example 1, said membrane being connected to the same cryogenic separation system using liquid nitrogen. The non-permeate (concentrated) stream from the membrane comprises:

$C_2F_6$ 15.66% vol.
$CHF_3$ 9.54% vol.
$CF_4$ 18.15% vol.
$N_2$ 56.65% vol.

at the same temperature and pressure as the feed stream, but at a flowrate of 12 sl/m.

The permeate stream from the membrane comprises:

$C_2F_6$ 0.02% vol.
$CHF_3$ 0.48% vol.
$CF_4$ 0.01% vol.
$N_2$ 99.49% vol.

The non-permeate stream is further sent to the cryogenic separation system disclosed in Example 1 and the following vapor and liquid streams are obtained:

Vapor Stream:

$C_2F_6$ 1.03% vol.
$CHF_3$ 0.69% vol.
$CF_4$ 16.5% vol.
$N_2$ 81.78% vol.

Liquid Stream $C_2F_6$ 47.83% vol.
$CHF_3$ 29.00% vol.
$CF_4$ 21.81% vol.
$N_2$ 1.37% vol.

The liquid stream is essentially concentrated into three liquid species $C_2F_6$, $CHF_3$ and $CF_4$. The liquid and vapor streams are e.g. treated as explained in Example 1.

Example 3

Under the same conditions as in Example 1, a feed stream comprising 0.20% vol. $C_2F_6$, 0.01% vol. $CHF_3$, 0.06% vol $CF_4$, 0.01% vol $NF_3$, 0.01% vol $SF_6$ and 99.71% vol nitrogen at a pressure of 714,286 Pascal, a temperature of 20° C. and a flowrate of 199 sl/m (standard liter per minute) is sent on the same membrane as in Example 1, said membrane being connected to the same cryogenic separation system using liquid nitrogen. The non-permeate (concentrated) stream from the membrane comprises:

$C_2F_6$ 0.5381% vol.
$CHF_3$ 0.02% vol.
$CF_4$ 0.1611% vol.
$NF_3$ 0.0245% vol.
$SF_6$ 0.0271% vol.
$N_2$ 99.2291% vol.

(At the same temperature and pressure than the feed stream, but at a flowrate of 73 sl/m.)

The permeate stream from the membrane comprises:

$C_2F_6$ 0.0041% vol.
$CHF_3$ 0.0047% vol.
$CF_4$ 0.0014% vol.
$NF_3$ 0.0016% vol.
$SF_6$ 0.0004% vol.
$N_2$ 99.9878% vol.

The pressure of the permeate is 6579 Pascal with a flowrate of 126 sl/m. The non-permeate stream is further sent to the cryogenic separation system disclosed in Example 1 (0.4335 pound of $LN_2$ for each pound of non-permeate stream) and the following vapor and liquid stream are obtained:

| Vapor Stream: | | |
| --- | --- | --- |
| $C_2F_6$ | 0.3418% vol. | Pressure: 714,286 Pascal |
| $CHF_3$ | 0.0125% vol. | Temperature: 144 K |
| $CF_4$ | 0.1592% vol. | Flowrate: 72.8 sl/m. |
| $NF_3$ | 0.0242% vol. | |
| $SF_6$ | 0.0118% vol. | |
| $N_2$ | 99.4505% vol. | |
| Liquid Stream | | |
| $C_2F_6$ | 85.9100% vol. | Pressure: 714,286 Pascal |
| $CHF_3$ | 3.2800% vol. | Temperature: 144 K |
| $CF_4$ | 0.9900% vol. | Flowrate: 0.2 sl/m. |
| $NF_3$ | 0.1400% vol. | |
| $SF_6$ | 6.6900% vol. | |
| $N_2$ | 2.9900% vol. | |

Example 4

Under the same conditions as in Example 1, a feed stream comprising 0.20% vol. $C_2F_6$, 0.01% vol. $CHF_3$, 0.06% vol $CF_4$, 0.01% vol $NF_3$, 0.01% vol $SF_6$ and 99.71% vol nitrogen at a pressure of 319,728 Pascal, a temperature of 20° C. and a flowrate of 170 sl/m (standard liter per minute) is sent on the same membrane as in Example 1, said membrane being connected to the same cryogenic separation system using liquid nitrogen. The non-permeate (concentrated) stream from the membrane comprises:

$C_2F_6$ 0.5600% vol.
$CHF_3$ 0.0200% vol.
$CF_4$ 0.1700% vol.
$NF_3$ 0.0300% vol.
$SF_6$ 0.0300% vol.
$N_2$ 99.2000% vol.

(At the same temperature and pressure than the feed stream, but at a flowrate of 112 sl/m.)

The permeate stream from the membrane comprises:

$C_2F_6$ 0.0154% vol.
$CHF_3$ 0.0041% vol.
$CF_4$ 0.0039% vol.
$NF_3$ 0.0019% vol.
$SF_6$ 0.0009% vol.
$N_2$ 99.9738% vol.

The pressure of the permeate is 6579 Pascal with a flowrate of 112 sl/m. The non-permeate stream is further sent to the cryogenic separation system disclosed in Example 1 (0.4335 lb. of $LN_2$ for each lb. of non-permeate stream) and the following vapor and liquid stream are obtained:

| Vapor Stream: | | |
| --- | --- | --- |
| $C_2F_6$ | 0.0072% vol. | Pressure: 714,286 Pascal |
| $CHF_3$ | 0.0003% vol. | Temperature: 144K |
| $CF_4$ | 0.1145% vol. | Flowrate: 72.8 sl/m. |
| $NF_3$ | 0.0197% vol. | |
| $SF_6$ | 0.0003% vol. | |
| $N_2$ | 99.8580% vol. | |
| Liquid Stream | | |
| $C_2F_6$ | 80.67% vol. | Pressure: 714,286 Pascal |
| $CHF_3$ | 2.88% vol. | Temperature: 144K |
| $CF_4$ | 8.21% vol. | Flowrate: 0.2 sl/m. |
| $NF_3$ | 1.52% vol. | |
| $SF_6$ | 4.34% vol. | |
| $N_2$ | 2.38% vol. | |

Example 5

Under the same conditions as in Example 2, a feed stream comprising 1.00% vol. $C_2F_6$, 0.01% vol. $CHF_3$, 0.01% vol. $CF_4$, and 98.96% vol. nitrogen at a pressure of 866,595 Pascal, a temperature of 20° C. and a flowrate of 5,000 sl/m (standard liter per minute) is sent on the same membrane (first membrane) as in Example 1, said membrane being connected to a second membrane (cascade connection: non-permeate side of the first to the feed side of the second).

The non-permeate (concentrated) stream from the first membrane comprises:

$C_2F_6$ 33.93% vol.
$CHF_3$ 0.17% vol.
$CF_4$ 0.31% vol.
$NF_3$ 0.17% vol.
$SF_6$ 0.31% vol.
$N_2$ 65.11% vol.

At the same temperature and pressure than the feed stream, but at a flowrate of 150 sl/m.

The permeate stream from the first membrane comprises:

$C_2F_6$ 0.0012% vol.
$CHF_3$ 0.0053% vol.
$CF_4$ 0.0009% vol.
$NF_3$ 0.0052% vol.
$SF_6$ 0.0009% vol.
$N_2$ 99.9865% vol.

The non-permeate (concentrated) stream from the second membrane comprises:

$C_2F_6$ 96.52% vol.
$CHF_3$ 0.23% vol.
$CF_4$ 0.81% vol.
$NF_3$ 0.24% vol.

SF$_6$ 0.81% vol.
N$_2$ 0.39% vol.

The permeate stream from the second membrane comprises:
C$_2$F$_6$ 0.0636% vol.
CHF$_3$ 0.1358% vol.
CF$_4$ 0.0424% vol.
NF$_3$ 0.1339% vol.
SF$_6$ 0.0406% vol.
N$_2$ 99.58739% vol.

Example 6

Under the same conditions as in Example 2, a feed stream comprising 1.00% vol. C$_2$F$_6$, 0.2% vol. CF$_4$, and 98.9% vol. nitrogen at a pressure of 213,315 Pascal, a temperature of 20° C. and a flowrate of 6,366 grams/min. is sent on the same membrane as in Example 1, said membrane being connected to a vacuum swing adsorption system (VSA) with a switching time of 15 min.

The non-permeate (concentrated) stream from the membrane comprises:
C$_2$F$_6$ 74.2% wt.
CF$_4$ 10.8% wt.
N$_2$ 15.1% wt.

At the same temperature and pressure than the feed stream, but at a flowrate of 84 grams/min.

The permeate stream from the membrane comprises:
C$_2$F$_6$ 0.001% wt.
CF$_4$ 0.014% wt.
N$_2$ 99.985% wt.

The VSA non-adsorbed stream comprises:
C$_2$F$_6$ 94.9% wt.
CF$_4$ 5.1% wt.

The VSA adsorbed stream comprises:
CF$_4$ 30.9% wt.
N$_2$ 69.1% wt.

Example 7

A system of the invention was used to recover PFCs from an effluent stream from a semiconductor tool. A first membrane separation unit included three hollow fiber bundles, while a second membrane separation unit included only one hollow fiber bundle. Each hollow fiber bundle was equal in surface area; thus the first membrane unit provided three times the surface area for mass transfer than did the first bundle. Each bundle also used the hollow fibers described in Example 1. A feed stream comprising 2083 ppm C$_2$F$_6$, 595 ppm CF$_4$, and balance nitrogen, at a pressure of about 540 kiloPascal, a temperature of 305K (32° C.) and a flowrate of 201 scfh, or 95 sl/m (standard liter per minute) was fed on the feed side of a polyimide membrane made according to U.S. Pat. No. 5,085,676. The PFC material balance indicated that the PFC flow in the feed was about 0.4590 scfh, or about 0.217 sl/m.; the product (non-permeate stream from the second membrane unit) had a PFC concentration of about 64.7%, and a nitrogen concentration of about 35.3%. The PFC recovered in the non-permeate from the second membrane was about 0.457 scfh, or 0.216 sl/m, for a PFC recovery of about 99.5%.

Further modifications to the invention will be apparent to those skilled in the art, and the scope of the following claims are not intended to be unfairly limited by the foregoing description.

What is claimed is:

1. A process for the separation and recovery of at least one perfluorocompound gas from a gas mixture containing at least one carrier gas and at least one perfluorocompound gas, said process comprising the steps of:
    (a) compressing a gas mixture contaning at least one carrier gas and at least one perfluorocompound gas;
    (b) heating said gas mixture to a temperature sufficient to selectively increase permeation of said at least one carrier gas;
    (c) contacting said gas mixture with one or more cascade connected membrane units which permeate said at least one carrier gas faster than said at least one perfluorocompound gas to obtain a permeate stream rich in said at least one carrier gas and a non-permeate stream rich in said at least one perfluorocompound gas;
    (d) passing said non-permeate steam to an adsorption system to produce an adsorbed stream comprising one or more adsorbed species and a non-adsorbed stream comprising one or more non-adsorbed species; and
    (e) recovering said adsorbed stream.

2. The process according to claim 1, further comprising recycling said permeate stream to step (a).

3. The process according to claim 1, which further comprises scrubbing said gas mixture to remove species harmful for the membrane units.

4. A process for the separation and recovery of at least one perfluorocompund gas from a gas mixture containing at least one carrier gas and at least one perfluorocompund gas, said process comprising the steps of:
    (a) compressing a gas mixture containing at least one carrier gas and at least one perfluorocompund gas;
    (b) heating said gas mixture to a temperature sufficient to selectively increase permeation of said at least one carrier gas;
    (c) contacting said gas mixture with one or more cascadde connected membrane units which permeate said at least one carrier gas faster than said at least one perfluorocompound gas to obtain a permeate stream rich in said at least one carrier gas and a non-permeate stream rich in said at least one perfluorocompound gas;
    (d) passing said non-permeate stream to a condensation system to produce a liquid stream rich in said at least one perfluorocompound gas and a vapor stream rich in said at least one carrier gas; and
    (e) recycling at least a portion of at least one of said permeate stream and said vapor stream.

5. The process according to claim 4, which further comprises scrubbing said gas mixture to remove species harmful for the membrane units.

6. A process for the separation and recovery of at least one perfluorocompound gas from a gas mixture containing at least one carrier gas and perfluorocompound gases, said process comprising the steps of:
    (a) compressing a gas mixture containing at least one carrier gas and two or more perfluorocompound gases;
    (b) heating said gas mixture to a temperature sufficient to selectively increase permeation of said at least one carrier gas;
    (c) contacting said gas mixture with one or more cascade connected membrane units which permeate said at least one carrier gas faster than said perfluorocompound gases to obtain a permeate stream rich in said at least one carrier gas and a non-permeate stream rich in said perfluorocompound gases;

(d) separating said two or more perfluorocompound gases in the non-permeate stream from each other by distillation; and (e) recycling at least a portion of said permeate stream to step (a).

7. The process according to claim 6, which further comprises scrubbing said gas mixture to remove species harmful for the membrane units.

* * * * *